United States Patent
Birman et al.

(10) Patent No.: US 12,161,594 B2
(45) Date of Patent: Dec. 10, 2024

(54) DECK EXTENSION ASSEMBLY

(71) Applicant: Stryker Corporation, Kalamazoo, MI (US)

(72) Inventors: Steven L. Birman, Kalamazoo, MI (US); David Scharich, III, Coloma, MI (US)

(73) Assignee: Stryker Corporation, Portage, MI (US)

( * ) Notice: Subject to any disclaimer, the term of this patent is extended or adjusted under 35 U.S.C. 154(b) by 340 days.

(21) Appl. No.: 17/849,901

(22) Filed: Jun. 27, 2022

(65) Prior Publication Data
US 2023/0050635 A1  Feb. 16, 2023

Related U.S. Application Data

(60) Provisional application No. 63/232,708, filed on Aug. 13, 2021.

(51) Int. Cl.
| *A61G 7/00* | (2006.01) |
| *A61B 5/00* | (2006.01) |
| *A61G 7/015* | (2006.01) |
| *A61G 7/018* | (2006.01) |

(52) U.S. Cl.
CPC .............. *A61G 7/015* (2013.01); *A61B 5/70* (2013.01); *A61G 7/018* (2013.01)

(58) Field of Classification Search
CPC .......... A61G 7/00; A61G 7/002; A61G 7/015; A61G 7/018; A61B 5/70
See application file for complete search history.

(56) References Cited

U.S. PATENT DOCUMENTS

| 2,452,366 | A | 10/1948 | Freund |
| 3,220,022 | A | 11/1965 | Nelson |
| 4,671,728 | A | 6/1987 | Clark et al. |
| 4,968,013 | A | 11/1990 | Kuck |
| 5,987,673 | A | 11/1999 | Smith |
| 6,212,714 | B1 | 4/2001 | Allen et al. |
| 6,968,584 | B1 | 11/2005 | Lafleche |
| 8,104,122 | B2 | 1/2012 | Richards et al. |
| 2012/0073052 | A1* | 3/2012 | Meyer ............ A61G 7/018 5/615 |
| 2016/0193095 | A1 | 7/2016 | Roussy et al. |
| 2017/0071806 | A1 | 3/2017 | Graves et al. |
| 2017/0143566 | A1 | 5/2017 | Elku et al. |
| 2019/0183702 | A1 | 6/2019 | Derenne et al. |
| 2020/0107982 | A1* | 4/2020 | Cutler ............ A61G 7/015 |

* cited by examiner

*Primary Examiner* — Fredrick C Conley
(74) *Attorney, Agent, or Firm* — Howard & Howard Attorneys PLLC

(57) ABSTRACT

A patient support apparatus includes a support frame that carries a patient support deck comprising a plurality of sections and a deck extension assembly including a deck extension frame that supports a deck extension section. The assembly is movable between an extended position and a retracted position. The support frame includes a deck rail defining a channel and a deck slot extending between a proximal and distal deck notch. The deck extension frame includes an extension rail that is moveably disposed in the channel and a frame slot. A latch link comprises a link slot and is moveably mounted to the deck extension frame. A latch pin is movably supported in each of the deck slot, frame slot, and link slot. The latch pin engages the distal deck notch when the assembly is in the extended position and the proximal deck notch when the assembly is in the retracted position.

20 Claims, 20 Drawing Sheets

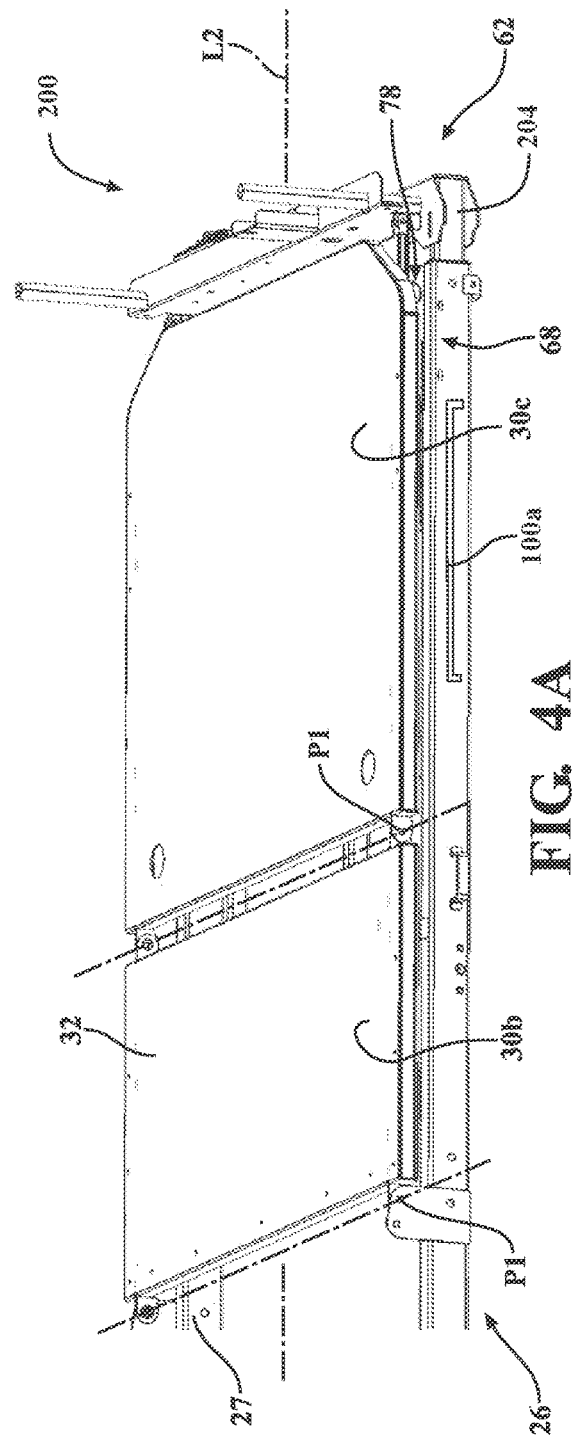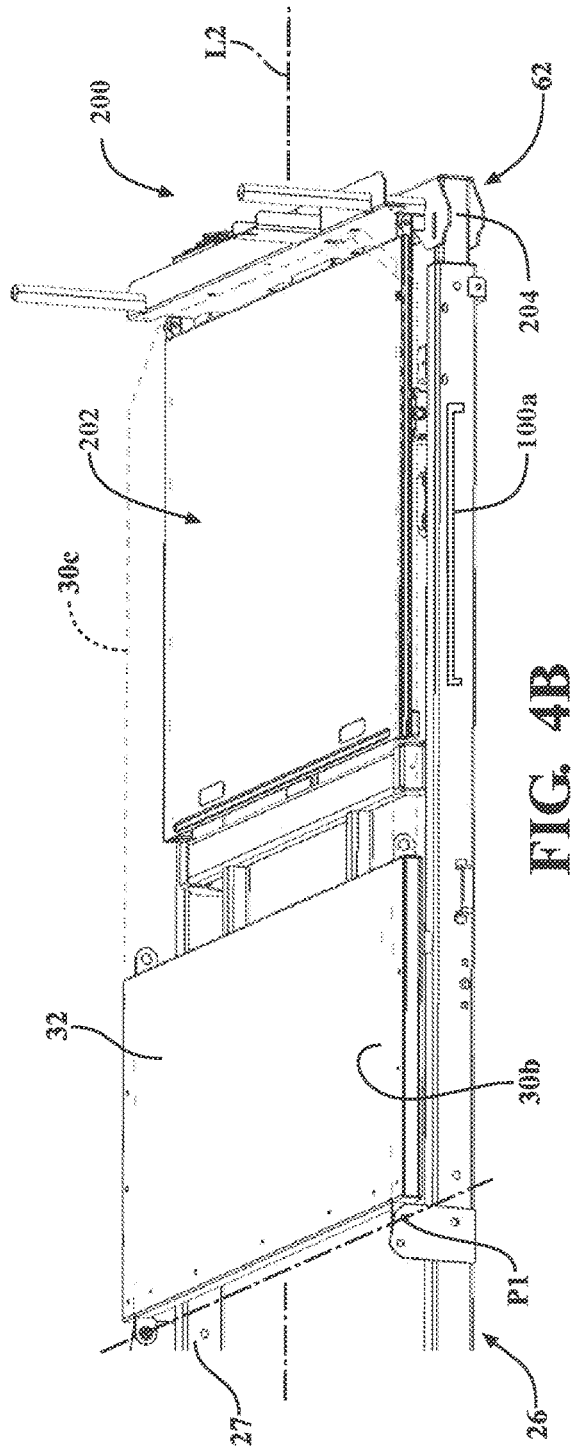

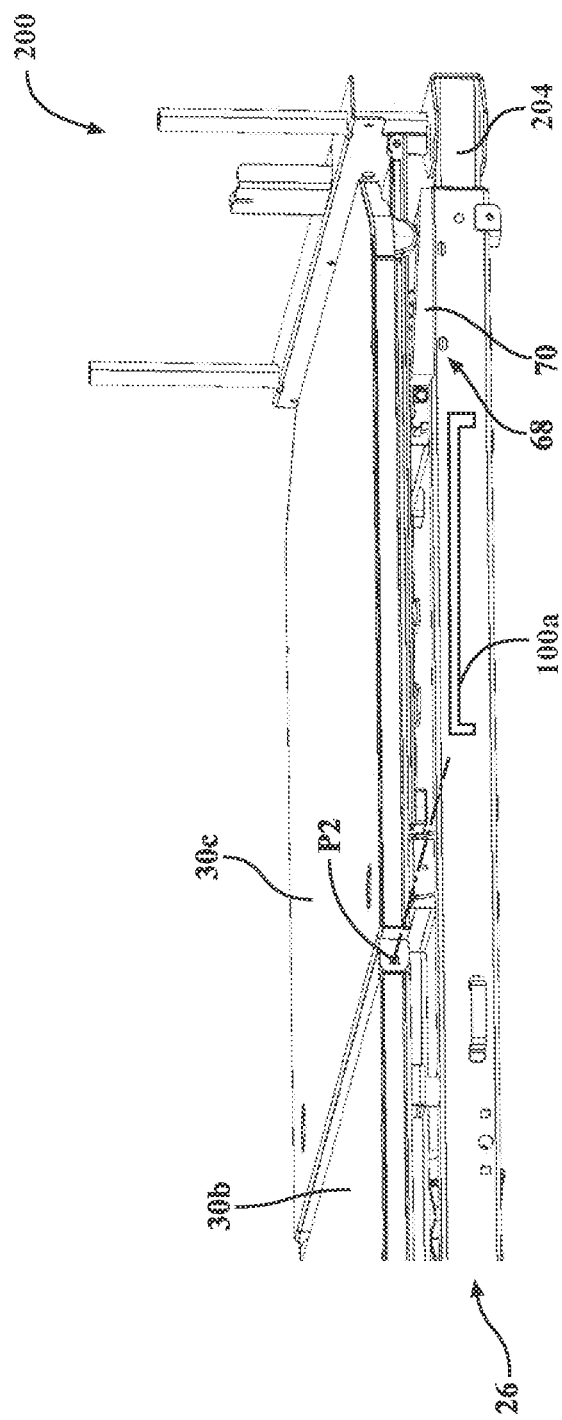

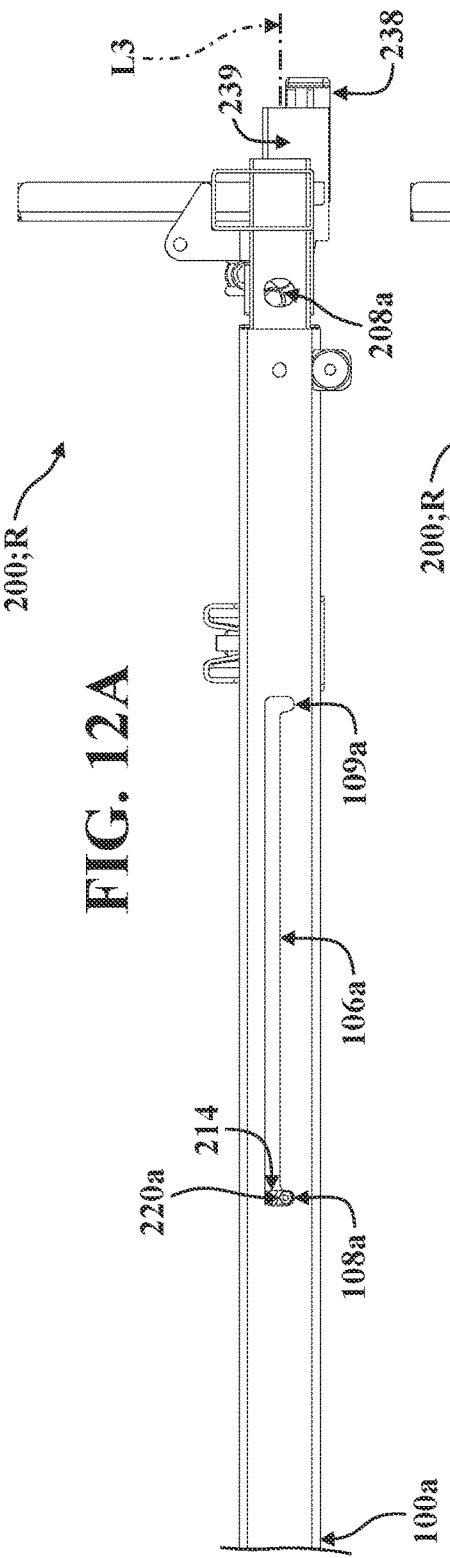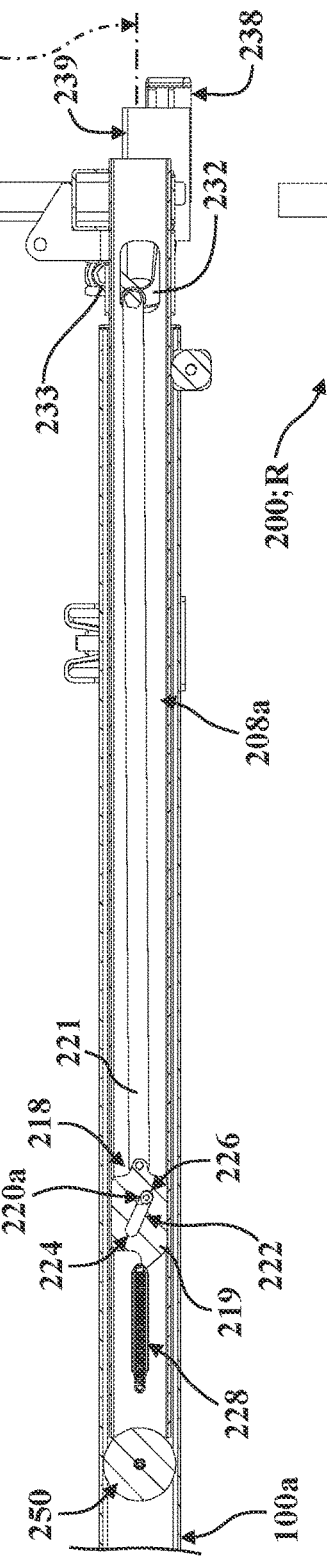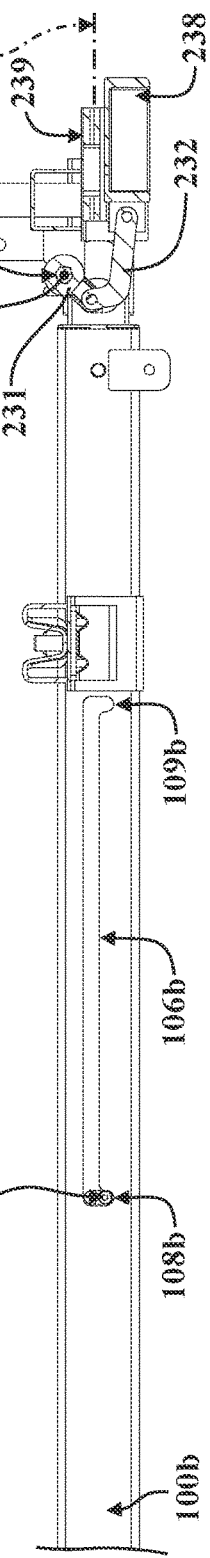
FIG. 12A  FIG. 12B  FIG. 12C

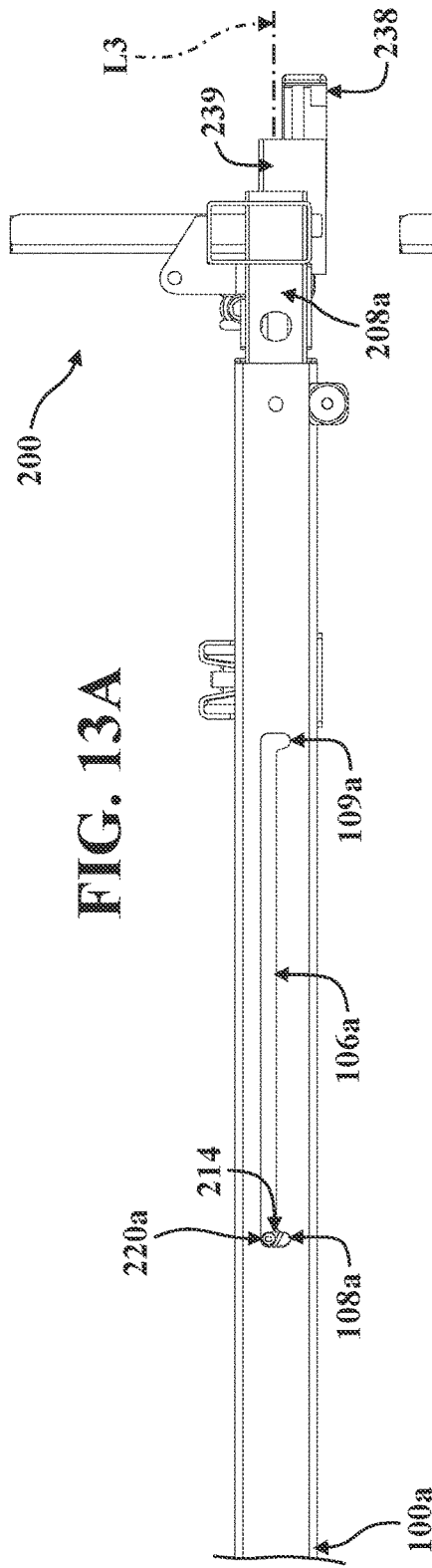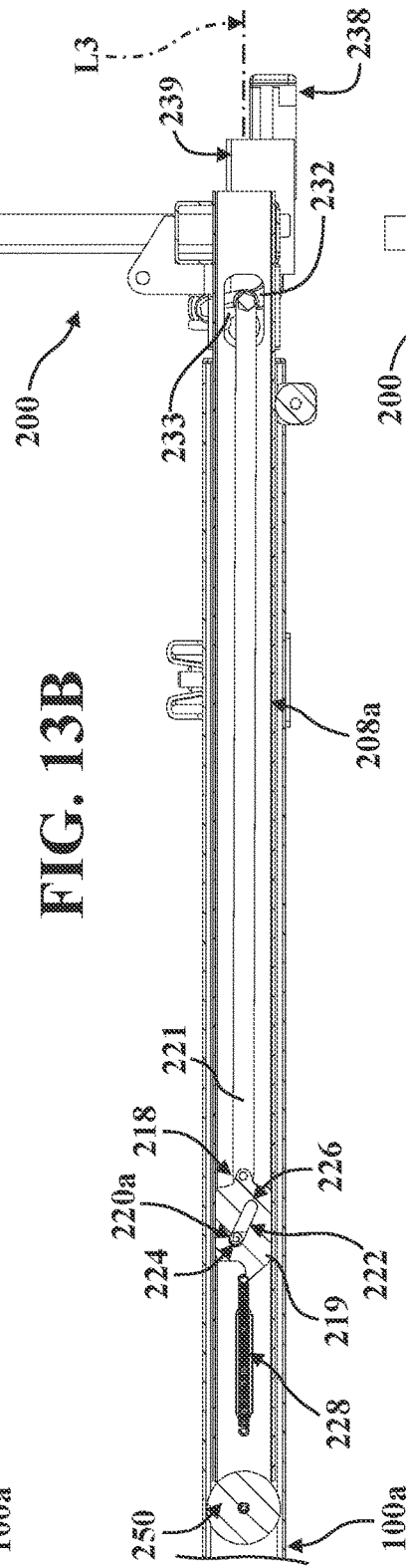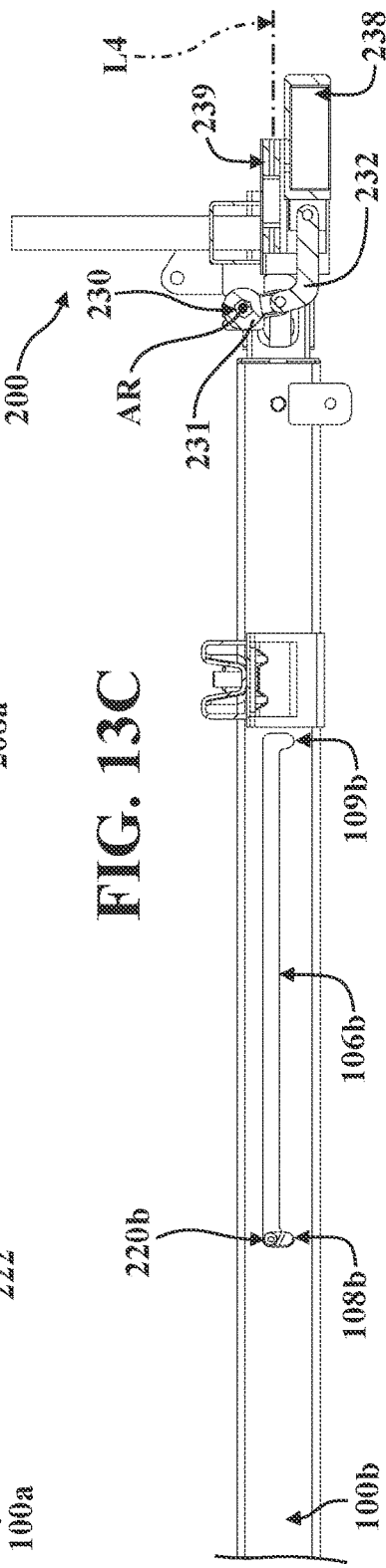

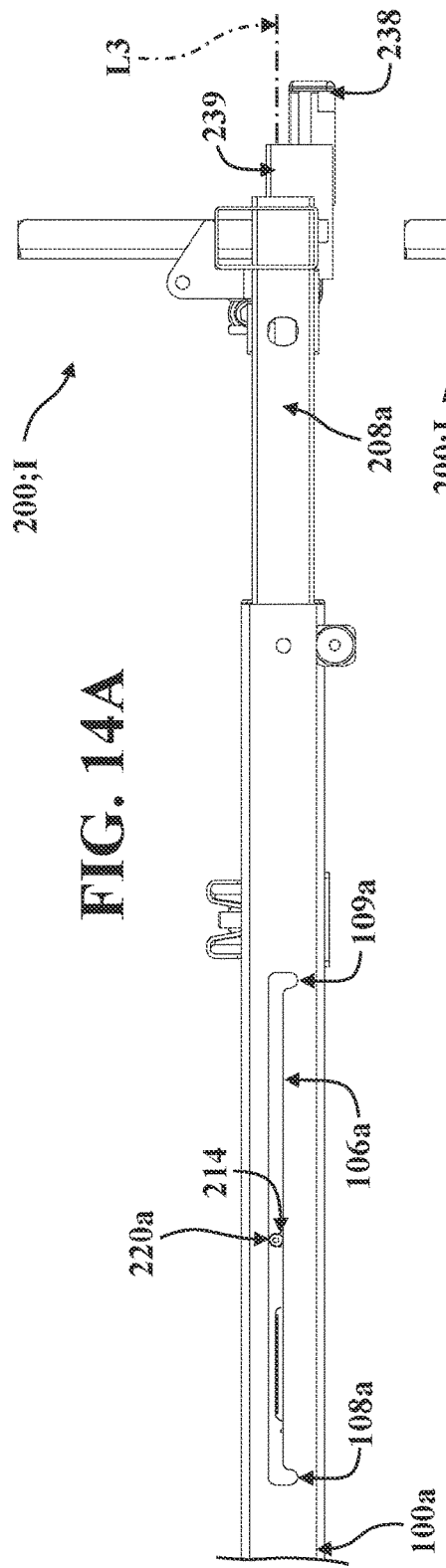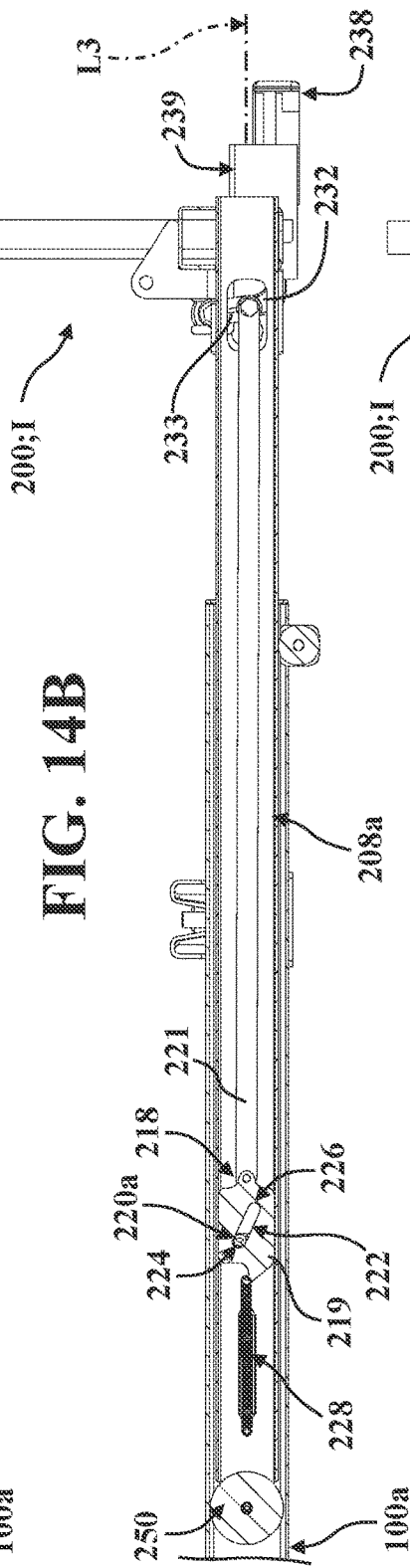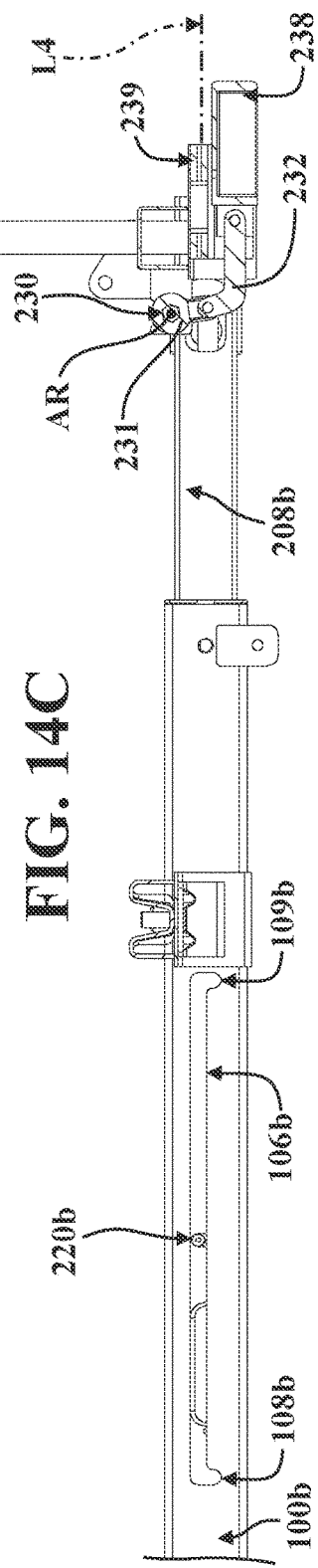

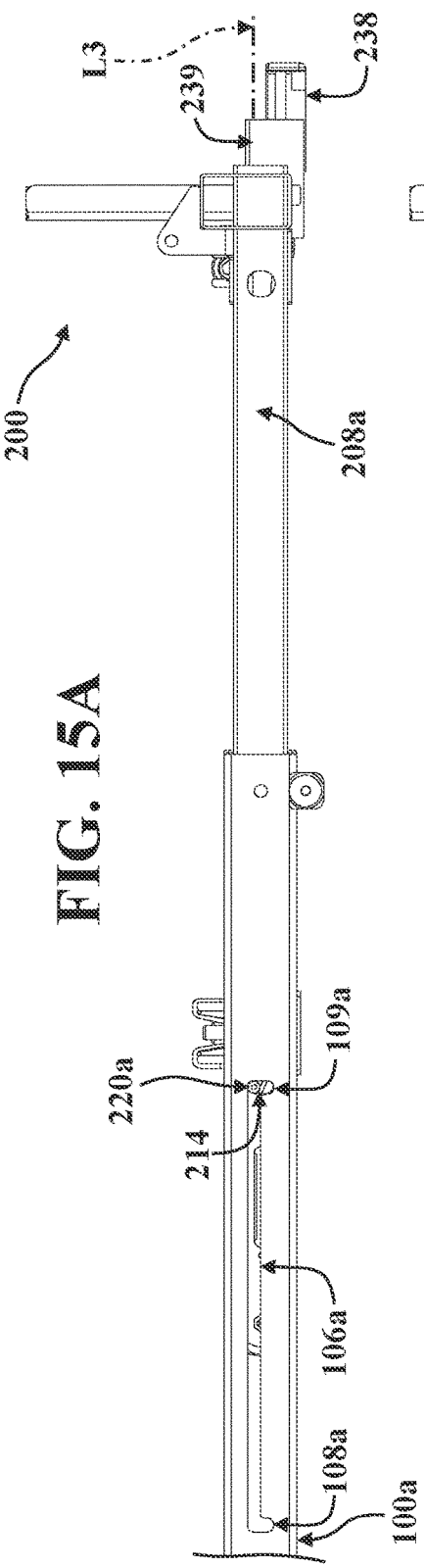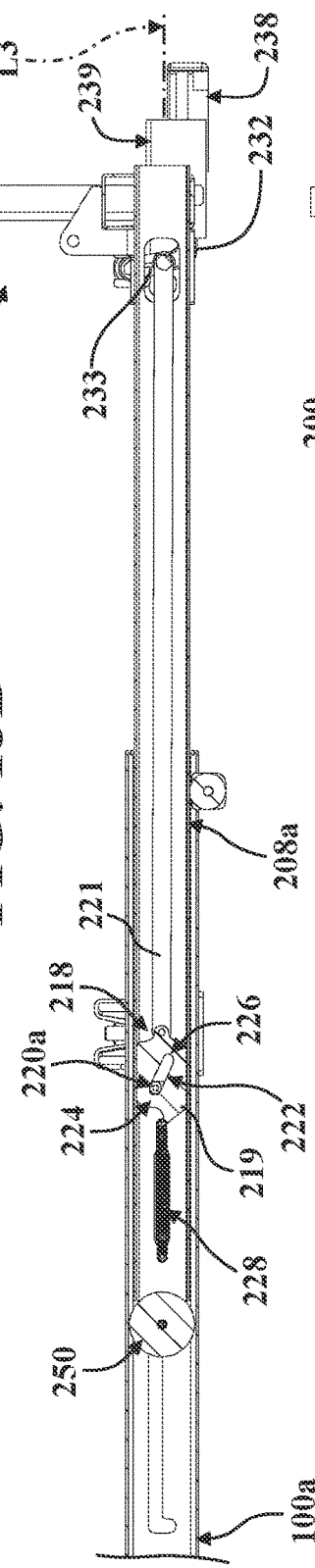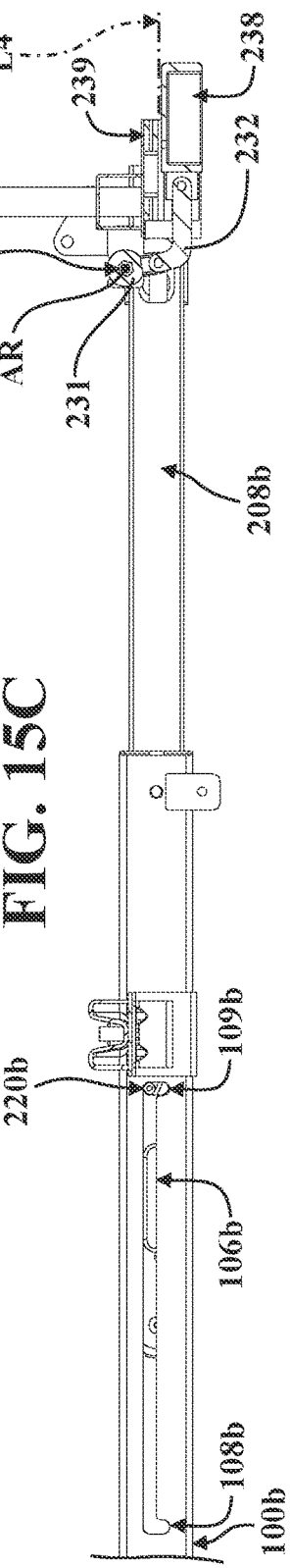

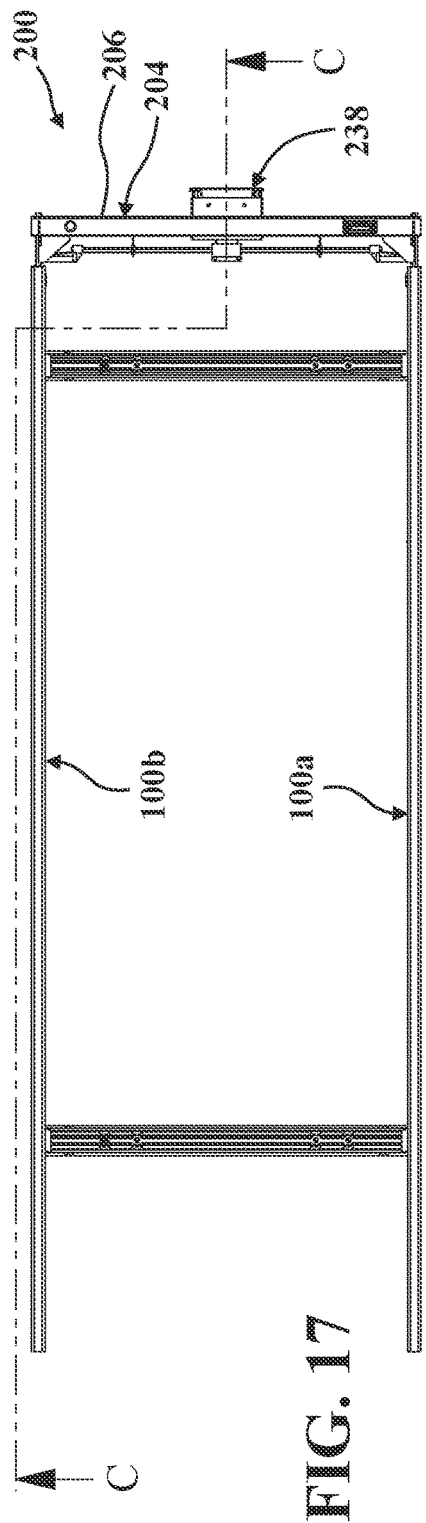
FIG. 17
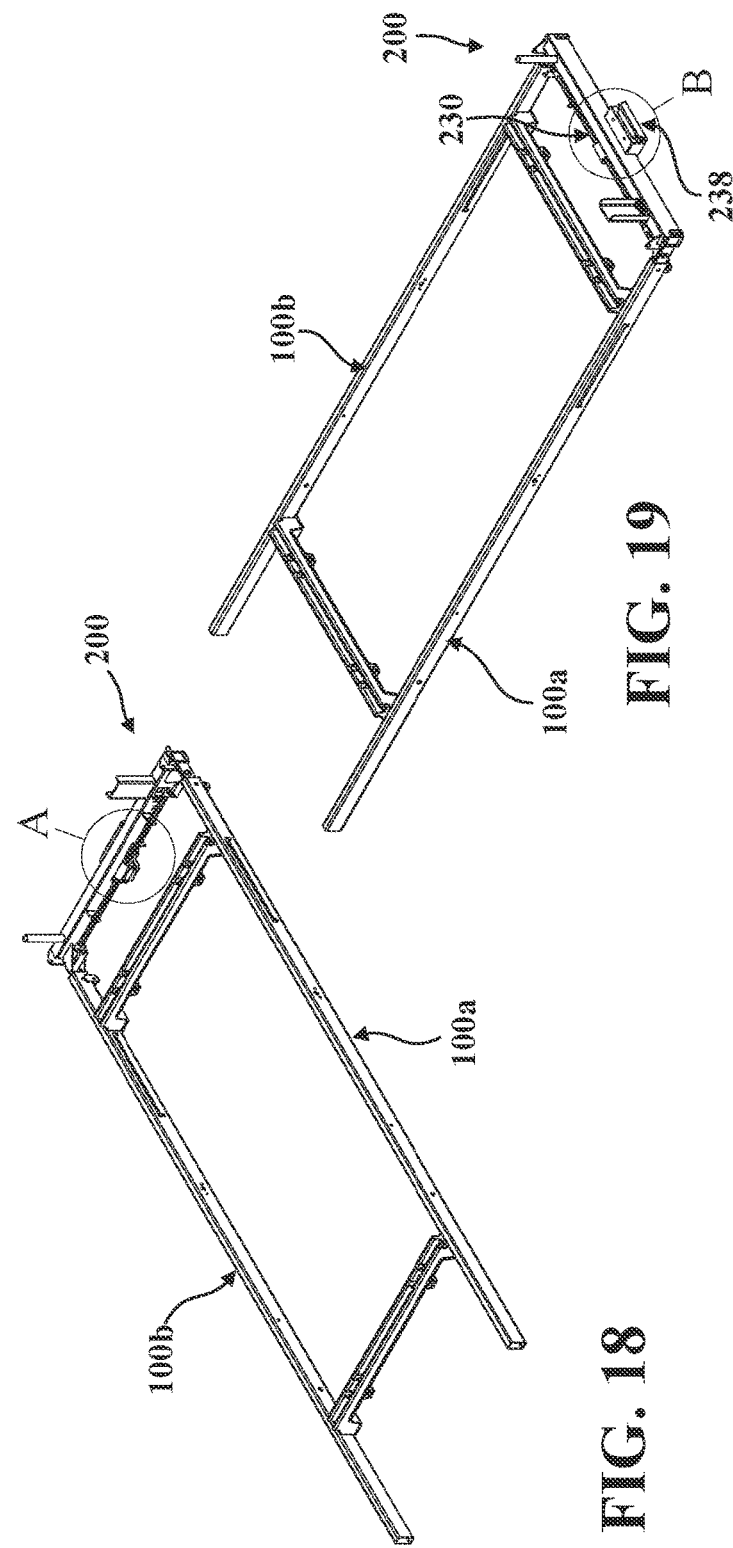
FIG. 18
FIG. 19

DECK EXTENSION ASSEMBLY

CROSS-REFERENCE TO RELATED APPLICATIONS

The subject patent application claims priority to, and all the benefits of, U.S. Provisional Patent Application No. 63/232,708, filed on Aug. 13, 2021, the entire contents of which are incorporated by reference herein.

BACKGROUND

Patient support apparatuses facilitate care of patients in a health care setting. Patient support apparatuses include, for example, hospital beds, stretchers, cots, tables, wheelchairs, and chairs. A conventional patient support apparatus comprises a base, a support frame having a patient support surface, and a patient support deck carried by the support frame. The patient support deck often has several articulating deck sections to place the patient in various configurations for treatment and/or comfort.

Occasionally, the patient support apparatus additionally comprises a deck extension assembly having a deck extension section that is arranged to extend and retract relative to the support frame. The deck extension section can be extended, for example, when taller patients are on the patient support apparatus—to extend an overall length of the patient support surface. Usually, the deck extension assembly comprises a pair of telescoping frame members that slide within a pair of support frame members. The deck extension section is fixed relative to the telescoping frame members and is arranged to slide along either an articulating foot section or the support frame. There is a need to secure the deck extension section in a retracted position and the extended position to avoid unwanted movement of the extension section. However, securing the deck extension section in either the retracted position or the extended position as well as freeing the deck extension section for movement between the retracted position and the extended positions can be time consuming and require physical exertion.

A patient support apparatus with a deck extension assembly designed to overcome one or more of the challenges above is desired.

SUMMARY

A patient support apparatus includes a support frame including a deck rail defining a channel disposed about a longitudinal axis and having a deck slot extending between a proximal deck notch and a distal deck notch. A patient support deck is carried by the support frame and may include a plurality of sections including a foot section. A deck extension assembly includes a deck extension section supported by a deck extension frame including an extension rail moveably disposed in the channel and having a frame slot, the deck extension assembly being selectively movable between an extended position to support the patient, and a retracted position. The deck extension assembly also includes a latch link include a link slot and is moveably mounted to the deck extension frame. The deck extension assembly also includes a latch pin movably supported in each of the deck slot, the frame slot, and the link slot, where the latch pin engages the proximal deck notch when the deck extension assembly is in the retracted position and engages the distal deck notch when the deck extension assembly is in the extended position. Force applied to the latch link moves the latch link relative to the deck extension frame to simultaneously bring the latch pin out of engagement with the proximal deck notch and into the deck slot to allow movement of the deck extension frame from the retracted position towards the extended position, or to simultaneously bring the latch pin out of engagement with the distal deck notch and into the deck slot to allow movement of the deck extension frame from the extended position towards the retracted position.

In another example, the patient support apparatus also includes a support frame including a deck rail defining a channel and having a deck slot extending along the deck rail between a proximal deck notch and a distal deck notch, each extending transversely into communication with the deck slot. A patient support deck is carried by the support frame and may include a plurality of sections including a foot section. A deck extension assembly including a deck extension section supported by a deck extension frame includes an extension rail moveably disposed in the channel and having a frame slot. The deck extension assembly is selectively movable along a longitudinal rail axis between an extended position for support of the patient, and a retracted position. The deck extension assembly also includes a latch link with a link slot and that is moveably mounted to the deck extension frame. The deck extension assembly also includes a latch pin movably supported in each of the deck slot, the frame slot, and the link slot. The latch pin engages the proximal deck notch when the deck extension assembly is in the retracted position and engages the distal deck notch when the deck extension assembly is in the extended position. Force applied to the latch link moves the latch link relative to the deck extension frame, and the link slot is arranged at an oblique angle relative to the longitudinal rail axis such that movement of the latch link drives the latch pin vertically and out of the proximal deck notch or the distal deck notch and into the deck slot to allow movement of the deck extension frame between the retracted and extended positions.

In yet another example, patient support apparatus also includes a support frame including a first deck rail defining a first channel disposed about a first longitudinal axis and having a deck slot formed extending along the first deck rail between a proximal deck notch and a distal deck notch, and a second deck rail defining a second channel disposed about a second longitudinal axis. A patient support deck is carried by the support frame and may include a plurality of sections including a foot section. A deck extension assembly is selectively movable between an extended position for support of the patient, and a retracted position. The deck extension assembly includes a deck extension section supported by a deck extension frame. The deck extension frame includes: a first extension rail defining a first frame slot and having a proximal first rail end and a distal first rail end; a second extension rail having a proximal second rail end and a distal second rail end; and a cross-member operatively attached to the first and second extension rails adjacent to the distal first and second rails ends of the first and second extension rails. The first and the second extension rails are respectively slidably supported in the first and the second channels of the first and second deck rails to allow the deck extension frame to extend relative to the patient support deck. A handle is operatively attached to the deck extension frame and arranged for movement in response to user engagement and engagement member disposed in communication with the handle and supported by the deck extension frame for rotation about an engagement axis in response to movement of the handle. A latch link including a link slot is operatively attached to the engagement member and to the first extension rail. A latch pin is movably supported in each of the deck slot, the first frame slot, and the link slot. The latch pin engages the proximal deck notch to secure the deck extension assembly in the retracted position, where rotation of the engagement member in response to force applied to the handle via user engagement articulates the latch link to simultaneously move the latch pin out of the proximal deck notch and into the link slot to allow movement of the deck extension frame from the retracted position toward the extended position.

The latch pin engages the distal deck notch to secure the deck extension assembly in the extended position, where rotation of the engagement member in response to force applied to the handle via user engagement articulates the latch link to simultaneously move the latch pin out of the proximal deck notch and into the link slot to allow movement of the deck extension frame from the extended position toward the retracted position.

In yet another example, a patient support apparatus includes a support frame including a deck rail defining a channel disposed about a longitudinal axis and having a deck guide extending between a proximal deck brace and a distal deck brace. A patient support deck is carried by the support frame and may include a plurality of sections. A deck extension assembly includes a deck extension section supported by a deck extension frame including an extension rail moveably disposed in the channel and having a frame guide, the deck extension assembly being selectively movable between an extended position and a retracted position. The deck extension assembly also includes a latch link include a link guide and is moveably mounted to the deck extension frame. The deck extension assembly also includes a latch pin supported for movement along each of the deck guide, the frame guide, and the link guide, where the latch pin engages the proximal deck brace when the deck extension assembly is in the retracted position and engages the distal deck brace when the deck extension assembly is in the extended position. Force applied to the latch link moves the latch link relative to the deck extension frame to simultaneously bring the latch pin out of engagement with the proximal deck brace and into engagement with the deck guide to allow movement of the deck extension frame from the retracted position towards the extended position, or to simultaneously bring the latch pin out of engagement with the distal deck brace and into engagement with the deck guide to allow movement of the deck extension frame from the extended position towards the retracted position.

BRIEF DESCRIPTION OF THE DRAWINGS

FIG. 4A is a top perspective view of a leg section and foot section of the patient support deck in a first configuration.

FIG. 4B is a top perspective view like FIG. 4, but with the foot section removed to show a deck extension section situated beneath the foot section.

FIG. 5 is a top perspective view of the leg section and foot section of the patient support deck in the first configuration illustrating engagement of a slider and bearing.

FIG. 12A a side view of the deck extension frame of the deck extension assembly of FIG. 11 latched in a retracted position.

FIG. 12B a cross-sectional view along B-B of the deck extension frame of the deck extension assembly of FIG. 11 latched in a retracted position.

FIG. 12C a cross-sectional view along C-C of the deck extension frame of the deck extension assembly of FIG. 11 latched in a retracted position.

FIG. 13A a side view of the deck extension frame of the deck extension assembly of FIG. 11 in a retracted position prior to extension of the deck extension frame.

FIG. 13B a cross-sectional view along B-B of the deck extension frame of the deck extension assembly of FIG. 11 in a retracted position prior to extension of the deck extension frame.

FIG. 13C a cross-sectional view along C-C of the deck extension frame of the deck extension assembly of FIG. 11 in a retracted position prior to extension of the deck extension frame.

FIG. 14A a side view of the deck extension frame of the deck extension assembly of FIG. 11 in an intermediate position during extension of the deck extension frame.

FIG. 14B a cross-sectional view along B-B of the deck extension frame of the deck extension assembly of FIG. 11 in an intermediate position during extension of the deck extension frame.

FIG. 14C a cross-sectional view along C-C of the deck extension frame of the deck extension assembly of FIG. 11 in an intermediate position during extension of the deck extension frame.

FIG. 15A a side view of the deck extension frame of the deck extension assembly of FIG. 11 in an extended position prior to latching in an extended position.

FIG. 15B a cross-sectional view along B-B of the deck extension frame of the deck extension assembly of FIG. 11 in an extended position prior to latching in an extended position.

FIG. 15C a cross-sectional view along C-C of the deck extension frame of the deck extension assembly of FIG. 11 in an extended position prior to latching in an extended position.

FIG. 17 a top perspective view of the deck extension frame of the deck extension assembly.

FIG. 18 is a first perspective view of the handle assembly of the deck extension assembly of FIG. 17.

FIG. 19 is a second perspective view of the handle assembly of the deck extension assembly of FIG. 17.

DETAILED DESCRIPTION

Figure 1:
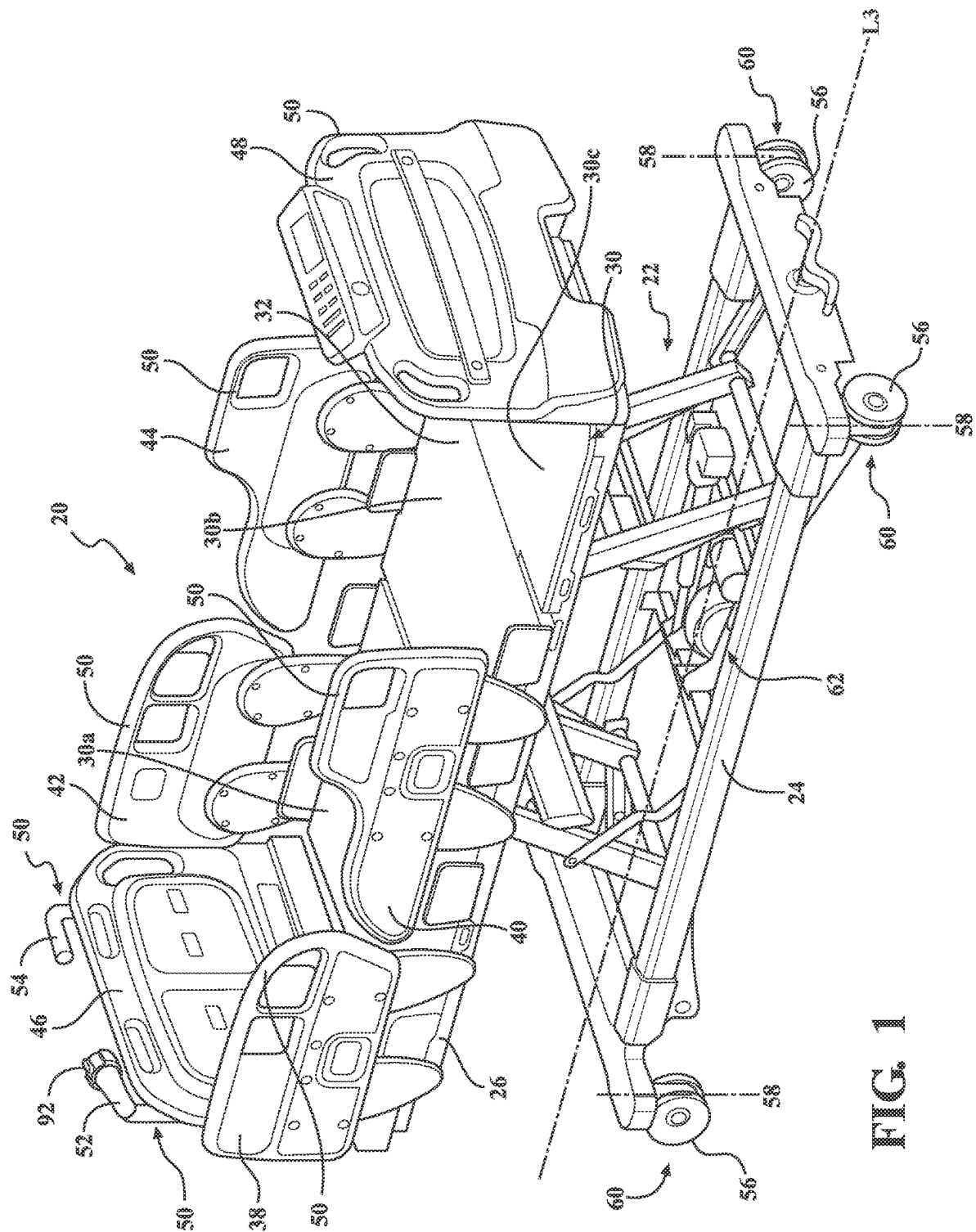
FIG. 1 is a perspective view of a patient support apparatus.

Referring to FIG. 1, a patient support apparatus 20 is shown for supporting a patient in a health care setting. The patient support apparatus 20 illustrated in FIG. 1 comprises a hospital bed. In other versions, however, the patient support apparatus 20 may comprise a cot, table, wheelchair, chair, or similar apparatus, utilized in the care of a patient.

A support structure 22 provides support for the patient. The support structure 22 illustrated in FIG. 1 comprises a base 24 and a support frame 26. The base 24 defines a first longitudinal axis L1 from a head end to a foot end. The support frame 26 is spaced above the base 24. The support structure 22 also comprises a patient support deck 30 disposed on and carried by the support frame 26. The patient support deck 30 comprises a plurality of sections, some of which articulate (e.g., pivot) relative to the support frame 26, such as a back section 30a, a leg section 30b, and a foot section 30c. The patient support deck 30 provides a patient support surface 32 upon which the patient is supported.

A mattress, although not shown, may be disposed on the patient support deck 30. The mattress comprises a secondary patient support surface upon which the patient is supported. The base 24, support frame 26, patient support deck 30, and patient support surface 32 each have a head end and a foot end corresponding to designated placement of the patient's head and feet on the patient support apparatus 20. The construction of the support structure 22 may take on any known or conventional design and is not limited to that specifically set forth above. In addition, the mattress may be omitted in certain versions, such that the patient rests directly on the patient support surface 32.

Side rails 38, 40, 42, 44 are supported by the base 24. A first side rail 38 is positioned at a right head end of the support frame 26. A second side rail 40 is positioned at a right foot end of the support frame 26. A third side rail 42 is positioned at a left head end of the support frame 26. A fourth side rail 44 is positioned at a left foot end of the support frame 26. If the patient support apparatus 20 is a stretcher, there may be fewer side rails. The first side rail 38 and the third side rail 42 may be mounted to the back section 30a to articulate with the back section 30a, while the second side rail 40 and the fourth side rail 44 are mounted to the support frame 26 to move with the support frame 26. Other arrangements are also possible. The side rails 38, 40, 42, 44 are movable between a raised position in which they block ingress and egress into and out of the patient support apparatus 20 and a lowered position in which they are not an obstacle to such ingress and egress. The side rails 38, 40, 42, 44 may also be movable to one or more intermediate positions between the raised position and the lowered position. In still other configurations, the patient support apparatus 20 may not comprise any side rails.

A headboard 46 and a footboard 48 are coupled to the support frame 26. In other versions, when the headboard 46 and footboard 48 are provided, the headboard 46 and footboard 48 may be coupled to other locations on the patient support apparatus 20, such as the base 24. In still other versions, the patient support apparatus 20 does not comprise the headboard 46 and/or the footboard 48.

User interfaces 50, such as handles, are shown integrated into the footboard 48 and side rails 38, 40, 42, 44 to facilitate movement of the patient support apparatus 20 over floor surfaces. Additional user interfaces 50 may be integrated into the headboard 46 and/or other components of the patient support apparatus 20. The user interfaces 50 are graspable by the user to manipulate the patient support apparatus 20 for movement.

Other forms of the user interface 50 are also contemplated. The user interface 50 may simply be a surface on the patient support apparatus 20 upon which the user logically applies force to cause movement of the patient support apparatus 20 in one or more directions, also referred to as a push location. This may comprise one or more surfaces on the support frame 26 or base 24. This could also comprise one or more surfaces on or adjacent to the headboard 46, footboard 48, and/or side rails 38, 40, 42, 44.

Support wheels 56 are coupled to the base 24 to support the base 24 on a floor surface such as a hospital floor. The support wheels 56 allow the patient support apparatus 20 to move in any direction along the floor surface by swiveling to assume a trailing orientation relative to a desired direction of movement. In the version shown, the support wheels 56 comprise four support wheels each arranged in corners of the base 24. The support wheels 56 shown are caster wheels able to rotate and swivel about swivel axes 58 during transport. Each of the support wheels 56 forms part of a caster assembly 60. Each caster assembly 60 is mounted to the base 24. Various configurations of the caster assemblies 60 are contemplated. In addition, in some versions, the support wheels 56 are not caster wheels and may be non-steerable, steerable, non-powered, powered, or combinations thereof. Additional support wheels 56 are also contemplated. A powered auxiliary wheel assembly may also be provided to transport the patient support apparatus 20 between locations.

Figure 2:
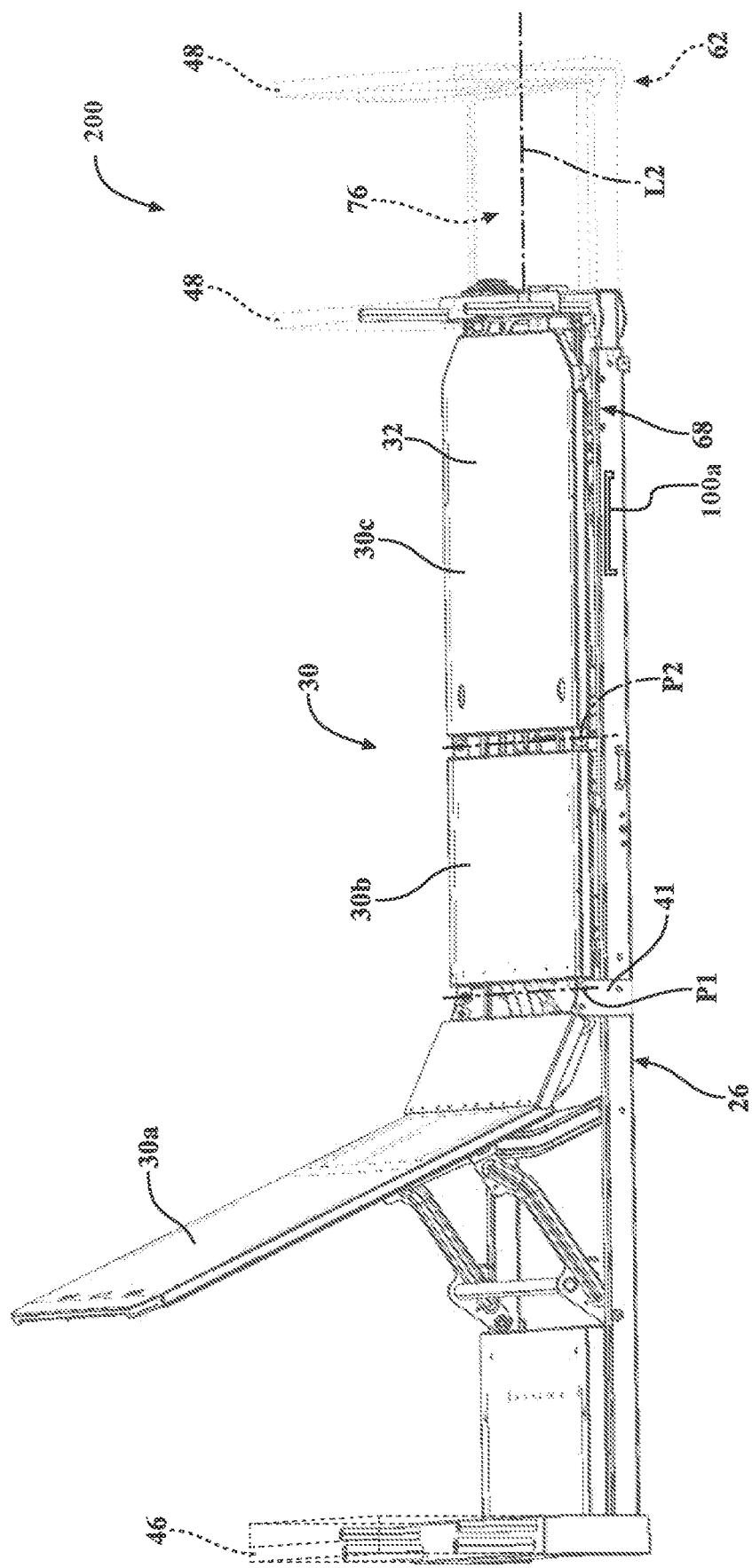
FIG. 2 is a perspective view of a support frame and patient support deck of the patient support apparatus of FIG. 1.

Referring to FIG. 2, the patient support deck 30 is shown supported and carried by the support frame 26. In particular, the deck sections 30a, 30b, 30c are shown in a configuration in which the back section 30a is raised above the support frame 26, the leg section 30b is in a lowered, horizontal position above the support frame 26, and the foot section 30c is in a lowered, horizontal position above the support frame 26.

The leg section 30b and the foot section 30c are pivotally coupled to each other and/or the support frame 26 at pivot joints defined about pivot axes P1, P2 as shown. Each of the deck sections 30a, 30b, 30c have a first end and a second end. It should be appreciated that the first and second ends are not necessarily the furthest extents of the deck sections but refer generally to opposite portions of the deck sections. The first end is closer to the head end of the patient support apparatus 20 when the patient support deck 30 is in a flat configuration and the second end is closer to the foot end of the patient support apparatus 20 when the patient support deck 30 is in the flat configuration. In the version shown, the first end of the leg section 30b is pivotally coupled to a bracket 41 fixed to the support frame 26 to pivot about the pivot axis P1. The first end of the foot section 30c is pivotally coupled to the second end of the leg section 30b to pivot about pivot axis P2. The leg section 30b and the foot section 30c may be pivotally coupled together by pivot pins, shafts, and the like at the pivot joints. Pivot brackets may be employed to form the pivot joints. Additionally, other types of connections are possible between the deck sections 30a, 30b, 30c so that the deck sections 30a, 30b, 30c can move, e.g., articulating, relative to one another. For instance, in some cases, translational joints may be provided between adjacent deck sections, or other compound movement connections may be provided between adjacent deck sections, such as joints that allow both pivotal and translational motion between adjacent deck sections.

Figure 3:
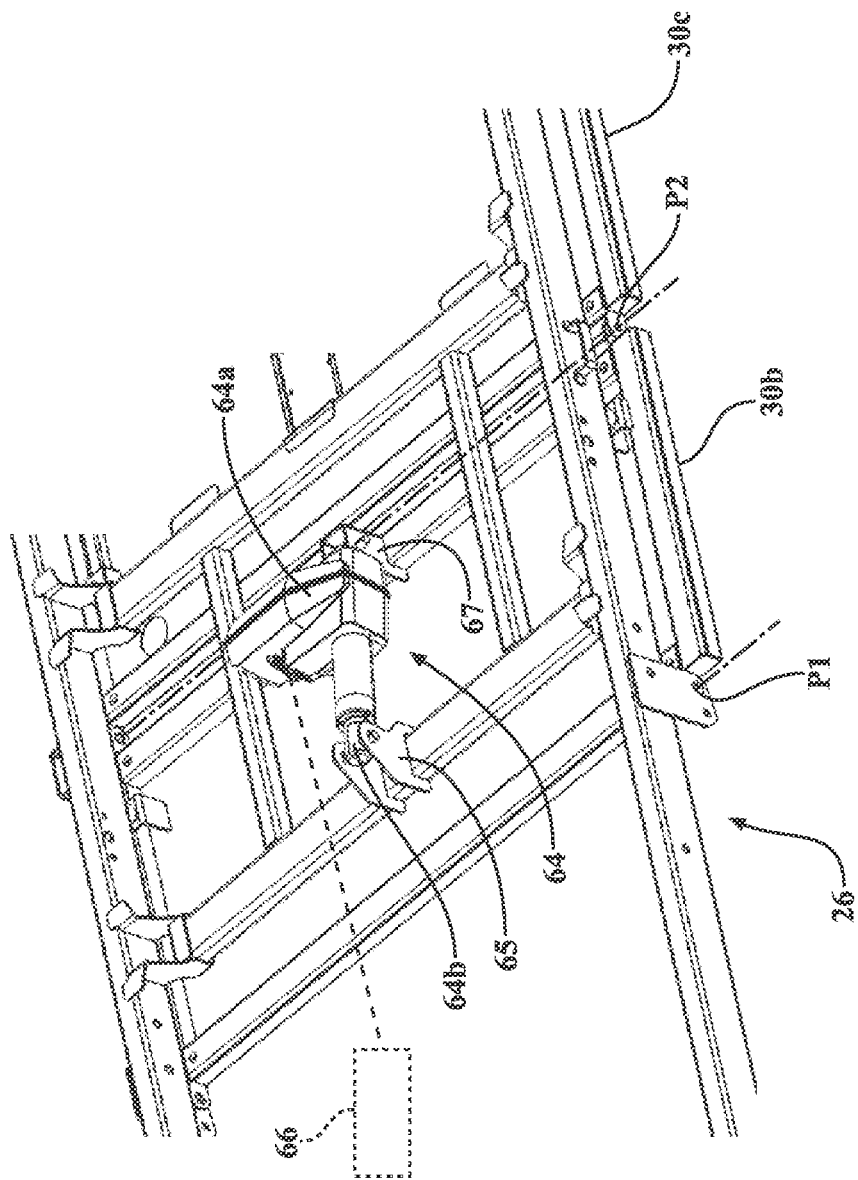
FIG. 3 is a bottom perspective view of a portion of the support frame and the patient support deck of FIG. 2.

Referring to FIG. 3, a leg section actuator 64 operates to move the leg section 30b and the foot section 30c. The leg section actuator 64 may be a linear actuator, rotary actuator, or other type of actuator capable of moving the leg section 30b and foot section 30c. The leg section actuator 64 may be electrically powered, hydraulic, electro-hydraulic, pneumatic, or the like. In the version shown, the leg section actuator 64 is an electrically powered linear actuator comprising an actuator housing 64a and drive rod 64b that extends and retracts with respect to the actuator housing 64a.

The leg section actuator 64 is operatively connected to the leg section 30b to pivot, or otherwise articulate, the leg section 30b relative to the support frame 26 between the lowered position and one or more raised positions. More specifically, the leg section actuator 64 pivots the leg section 30b about pivot axis P1 relative to the support frame 26. Owing to the pivotal coupling of the second end of the leg section 30b to the first end of the foot section 30c at pivot axis P2, when the leg section 30b is moved, the first end of the foot section 30c is also moved. Thus, the leg section actuator 80 also operates to articulate the foot section 30c relative to the support frame 26 between the lowered position and one or more raised positions. In the version shown, the leg section actuator 64 is pivotally connected at a first actuator end to a mounting bracket 65 fixed to the support frame 26. The leg section actuator 64 is pivotally connected at a second actuator end to a mounting bracket 67 fixed to the leg section 30b. The leg section actuator 64 could be pivotally connected to these brackets via pivot pins, shafts, and the like. In other versions, the leg section actuator 64 may be connected through other types of connections or linkages to move the leg section 30b to the lowered position or the one or more raised positions.

The leg section actuator 64 is operable to move the leg section 30b and the foot section 30c to different configurations. For example, the leg section 30b and foot section 30c may be placed in a flat configuration in which a patient would lie flat on the patient support deck 30 (see FIG. 4A). In this configuration, the leg section 30b and foot section 30c are aligned parallel to a second longitudinal axis L2 defined by the support frame 26. The leg section 30b and foot section 30c may also be placed in a raised configuration in which a patient's knee would be partially elevated (see FIG. 5B). To reach this configuration, the leg section actuator 64 has been operated to partially extend the drive rod 64b from the housing 64a.

A control system is provided to control operation of the actuator 64 (and other actuators not shown). The control system comprises a controller 66 (see FIG. 3) having one or more microprocessors for processing instructions or for processing an algorithm stored in memory to control operation of the actuator 64 (and other actuators not shown) to move the leg section 30b and the foot section 30c. Additionally, or alternatively, the controller 66 may comprise one or more microcontrollers, field programmable gate arrays, systems on a chip, discrete circuitry, and/or other suitable hardware, software, or firmware that can carry out the functions described herein. The controller 66 may be carried on-board the patient support apparatus 20 or may be remotely located. In one version, the controller 66 is mounted to the base 24. In other versions, the controller 66 is mounted to one or more of the support frame 26, the side rails 38, 40, 42, 44, the headboard 46, the footboard 48, or any other location. Power to the actuators and/or the controller 66 may be provided by a battery power supply or an external power source. The user, such as a caregiver, may actuate a user input device (not shown), which transmits a corresponding input signal to the controller 66, and the controller 66 controls operation of the actuator 64 based on the input signal.

Referring to FIGS. 4A and 4B, a deck extension assembly 200 according to versions of the present disclosure is shown. The deck extension assembly 200 comprises a deck extension section 202 (see FIG. 4B). The deck extension assembly 200 is provided to extend and retract relative to the support frame 26 to adjust an overall length of the patient support surface 32 that is available to support the patient. For example, when patients of different heights are using the patient support apparatus 20, the deck extension assembly 200 can be adjusted to accommodate such patients. Extension of the deck extension assembly 200 along the second longitudinal axis L2 is shown by broken lines in FIG. 2. The deck extension assembly 200 is selectively movable between an extended position E to support the patient, and a retracted position R. When the deck extension assembly 200 is in the retracted position R, and the foot section 30c is in the lowered position, the deck extension section 202 is substantially disposed beneath the foot section 30c (compare FIGS. 4A and 4B—the foot section 30c has been hidden in FIG. 4B). However, when the deck extension assembly 200 is in the extended position E, as shown by broken lines in FIG. 2, the deck extension section 202 is extended out from beneath the foot section 30c to provide additional patient support surface. Referring to FIG. 5, in some examples, one or more bearings 68 are arranged to act between the foot section 30c and the support frame 26 when the foot section 30c articulates relative to the support frame 26. In the example shown, the bearings 68 are mounted to the support frame 26 and are thereby fixed to the support frame 26. In other versions, the bearings 68 may be movable or fixed to another component of the patient support apparatus 20. In the version shown, the second end of the foot section 30c is configured to slide along the bearings 68. One bearing 68 is shown in FIG. 5, but a similar bearing 68 is present on an opposite side of the support frame 26.

Each of the bearings 68 may comprise a bearing block 70 formed at least partially of plastic. For instance, the bearing blocks 70 may be formed of polyamides or nylon, high-density polyethylene (HDPE), low-density polyethylene (LDPE), polyethylene terephthalate (PET), polypropylene (PP), high impact polystyrene (HIPS), polyvinyl chloride (PVC), polytetrafluoroethylene (PTFE), combinations thereof, or other suitable plastic materials. The bearing blocks 70 may also be formed of other materials, such as metal, combinations of metal and plastic, etc. The bearing blocks 70 are fixed to the support frame 26 via one or more fasteners, adhesive, welding, or the like to be spaced from each other on opposing deck rails 27 the support frame 26. The bearing blocks 70 may further be coated with low friction coatings to reducing frictional forces between the bearing blocks 70 and the foot section 30c, such as a polytetrafluoroethylene (PTFE) coating or other suitable low friction coating.

Figure 6:
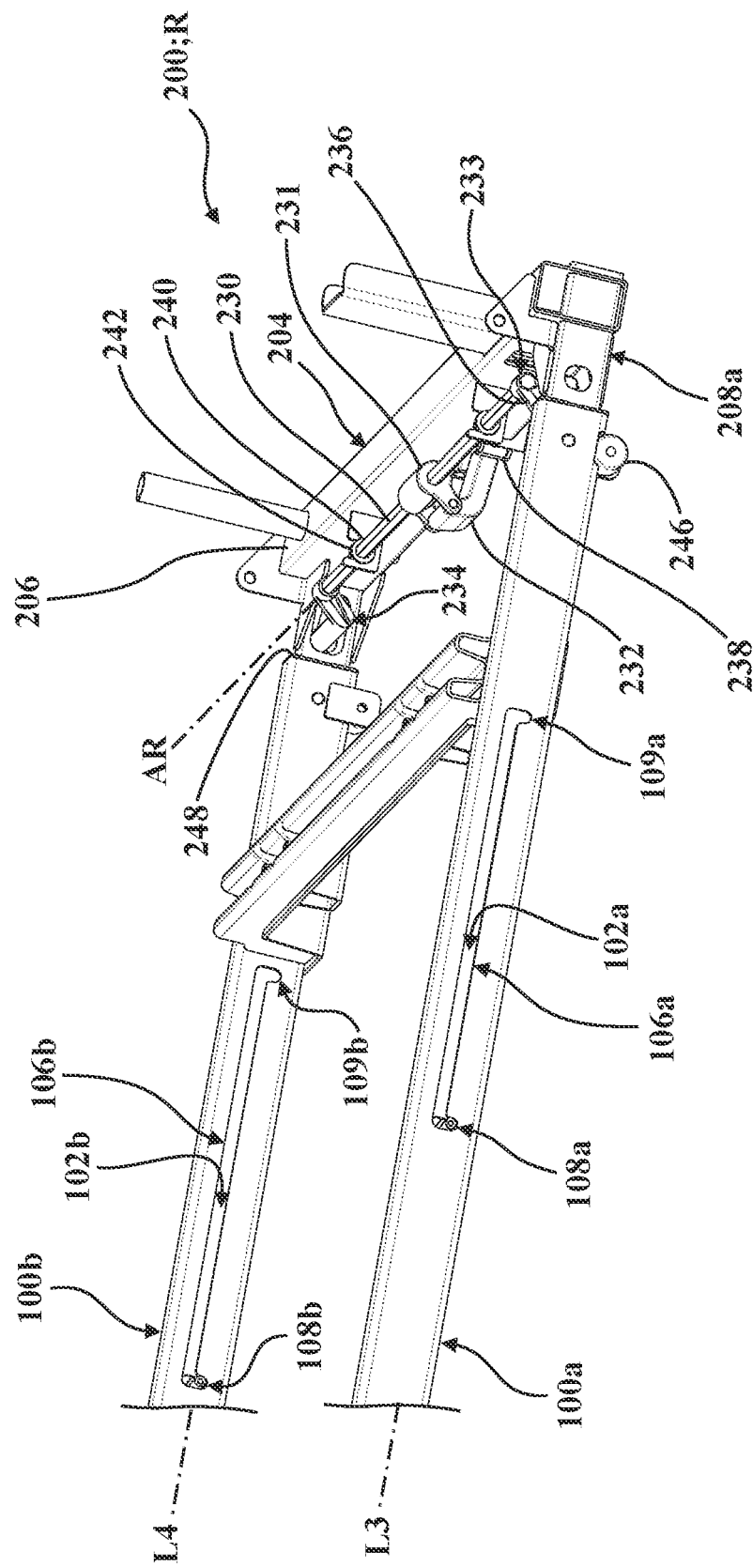
FIG. 6 is a top perspective view of a support frame comprising a pair of opposing deck rails and a deck extension frame including a cross-member and opposing extension rails that are moveable disposed in the pair of opposing deck rails.
Figure 7:
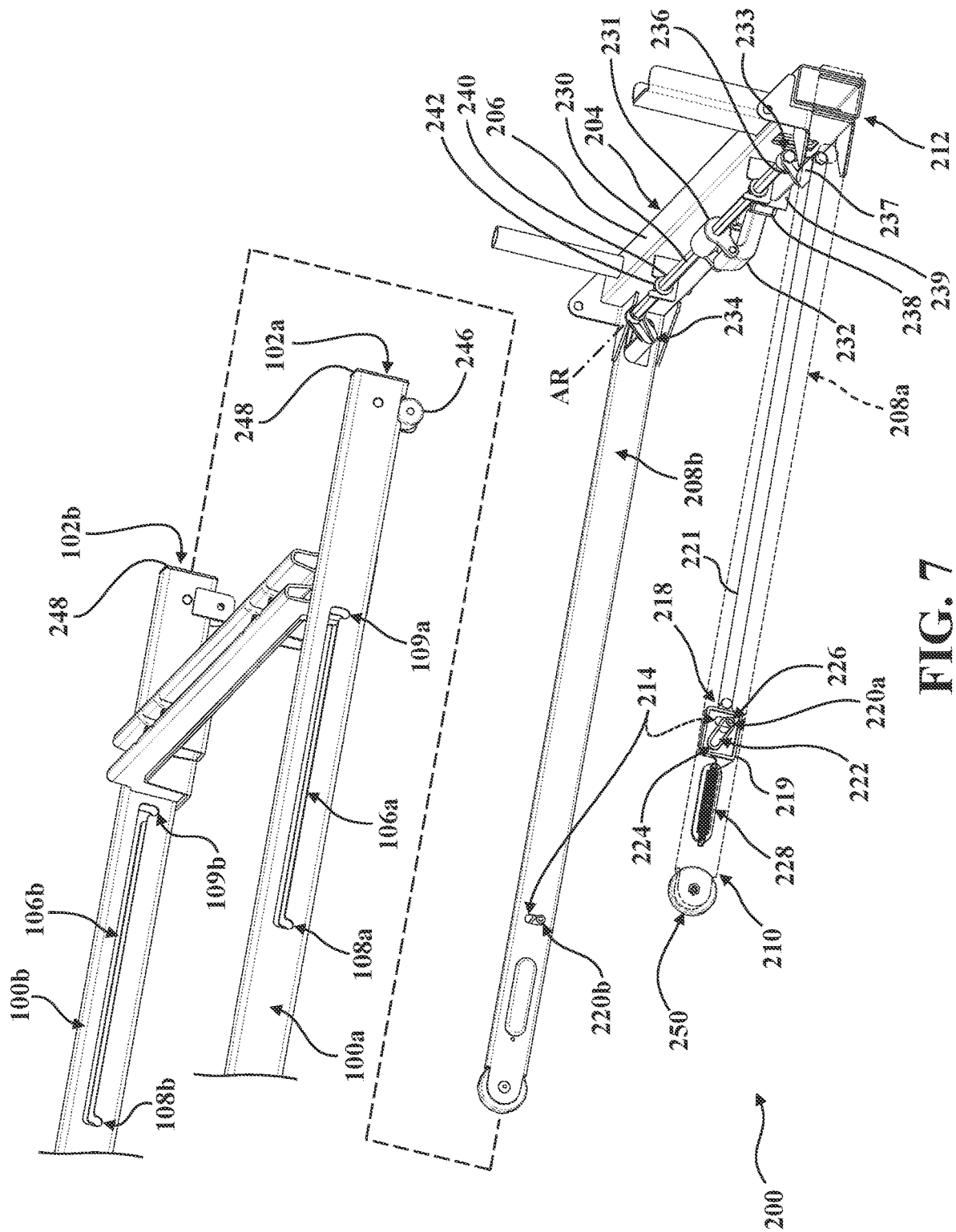
FIG. 7 is a partially exploded view of FIG. 6 illustrating a deck rail, an extension rail, and a latch link.

Referring an example of the deck extension assembly 200 illustrated in FIG. 6, the deck extension section 202 is supported by a deck extension frame 204 including a cross-member 206 and opposing extension rails 208a, 208b. In FIG. 7, which is a partially-exploded view of the example deck extension assembly 200 of FIG. 6, certain components of the deck extension assembly 200 are shown in phantom outline for illustrative purposes.

Referring now to FIGS. 6 and 7, the deck extension assembly 200 illustrated cooperates with the support frame 26, which includes a pair of opposing deck rails 27 as noted above. In this example, the deck rails 27 include a first deck rail 100a and a second deck rail 100b. The first deck rail 100a defines a first channel 102a disposed about a longitudinal axis L3. The first deck rail 100a has an inner wall and an outer wall (not shown in detail). A first deck slot 106a (also referred to herein as a first "deck guide") is defined by the inner wall, the outer wall, or both of the inner wall and the outer wall. In the illustrated versions, the inner wall and the outer wall of the first deck rail 100a define the first deck slot 106a extending between a first proximal deck notch 108a (also referred to herein as a first "proximal deck brace") and a first distal deck notch 109a (also referred to herein as a first "distal deck brace") which define the retracted position R and the extended position E, respectively. In some versions (not shown in detail), additional notches (or braces) may be arranged between the first proximal deck notch 108a and the first distal deck notch 109a to place the deck extension assembly 200 in one or more intermediate positions I. Other configurations are contemplated.

In the illustrated versions, the first deck slot 106a extends parallel to the longitudinal axis L3 and the first proximal deck notch 108a and the first distal deck notch 109a extend downward (towards the floor) from, and perpendicular to, the longitudinal axis L3. The second deck rail 100b defines a second channel 102b disposed about a longitudinal axis L4. In the illustrated versions, the second deck rail 100b defines a second deck slot 106b extending between a second proximal deck notch 108b and a second distal deck notch 109b. However, as will be appreciated from the description below, the deck extension assembly 200 could be configured to operate with only the first deck slot 106a. In this example, the second deck slot 106b extends parallel to the longitudinal axis L4 and the second proximal deck notch 108b and the second distal deck notch 109b downward from (towards the floor), and perpendicular to, longitudinal axis L4. Said differently, in some versions, the second deck rail 100b may not define the second deck slot 106b extending between the second proximal deck notch 108b and the second distal deck notch 109b.

It should be appreciated that the use of the terms "proximal" and "distal" with respect to the deck extension assembly 200 and the components thereof, as well as the opposing deck rails 100 of the support frame 26 that the deck extension assembly 200 cooperates with, refer generally to opposite ends, portions, and/or features of these components. For the purposes of clarity and consistency, the term "proximal" is used to describe an end, portion, and/or feature that is closer to the head end of the patient support apparatus 20 when the patient support deck 30 is in a flat configuration, and the term "distal" is used to describe an end, portion, and/or feature that is closer to the foot end of the patient support apparatus 20 when the patient support deck 30 is in the flat configuration.

Referring now to FIG. 6, the opposing extension rails 208a, 208b are moveably disposed in the first and the second channels 102a, 102b of the first and second deck rails 100a, 100b of the support frame 26. To this end, the first extension rail 208a is moveable in the first channel 102a along the longitudinal axis L3 and the second extension rail 208b is moveable in the second channel 102b along the longitudinal axis L4 such that the deck extension assembly 200 is selectively movable along the along the second longitudinal axis L2 between the extended position E and the retracted position R. The first extension rail 208a has a proximal first rail end 210 and a distal first rail end 212 (see FIG. 7), and the second extension rail 208b has a proximal second rail end and a distal second rail end (not shown in detail). In this example, the cross-member 206 extends between the first extension rail 208a and the second extension rail 208b. More specifically, the cross-member 206 is operatively attached to the first and second extension rails 208a, 208b adjacent to the distal first rail end 212 and the distal second rails end, respectively. The first extension rail 208a includes a first frame slot 214 (also referred to herein as a first "frame guide"). In the illustrated version, the first frame slot 214 is substantially perpendicular to the longitudinal axis L3 defined by the first channel 102a of the first deck rail 100a. In such an example, the first frame slot 214 extends perpendicular to the longitudinal axis L3 and has an upper and a lower end (not shown in detail).

While not shown in detail herein, it will be appreciated that each of the deck rails 100a, 100b and/or each of the extension rails 208a, 208b, may include or otherwise define components and/or structural features. Here, for the purposes of clarity and consistency, aspects of the second deck rail 100b and/or the second extension rail 208b may generally be applied to corresponding aspects of the first deck rail 100a and/or the first extension rail 208a, and are not necessarily identified with reference numerals herein or throughout the drawings. For example, in the illustrated versions, like the first frame slot 214 described above, a second frame slot is formed extending perpendicular to the longitudinal axis L4 defined by the second channel 102b of the second deck rail 100b. In such an example, the second frame slot extends perpendicular to the longitudinal axis L3 and has an upper and a lower end. In some versions, the second deck rail 100b may not define the second frame slot.

With specific reference to the FIG. 7, the deck extension assembly 200 also includes a first latch link 218 and a first latch pin 220a. The first latch link 218 and the first latch pin 220a cooperate with: the first frame slot 214 of the first extension rail 208a; and the first proximal deck notch 108a, the first deck slot 106a, and the first distal deck notch 109a of the first deck rail 100a, to latch and release the deck extension assembly 200 in the extended position E or the retracted position R, and allow movement of the deck extension assembly 200 between the extended position E and the retracted position R.

Referring again to FIG. 7 (see also FIG. 12B), the first latch link 218 comprises a first card 219 in which a first link slot 222 (also referred to herein as a first "link guide") is defined, and a first link arm 221. The first card 219 is pivotably coupled to the first link arm 221 in the illustrated version, and is slidably disposed within the first extension rail 208a. The first link slot 222 defined in the first card 219 has a first upper link slot end 224, and a first lower link slot end 226. In some versions, the first link slot 222 slot extends across the longitudinal axis L3 and has the first upper link slot end 224 above the longitudinal axis L3 and the first lower link slot end 226 below the longitudinal axis L3. In the illustrated versions, the first link slot 222 extends across the longitudinal axis L3 with the first upper link slot end 224 above the longitudinal axis L3 in a proximal position and the first lower link slot end 226 below the longitudinal axis L3 in a distal position. In some versions, the first link slot 222 extends across the longitudinal axis at a first angle A1 of from 10° to 80°. Further, the first latch link 218 is moveably mounted to the deck extension frame 204. In the illustrated versions, a proximal first link end of the first latch link 218 is coupled to the proximal first rail end 210 of the first extension rail 208a. The first latch link 218 is coupled to the first extension rail 208a with a first biasing element 228, e.g., a spring. More specifically, the first card 219 is slidably supported in the first extension rail 208a, and the first biasing element 228 is coupled between the first card 219 and the first extension rail 208a. In this example, the first latch link 218 is biased in a proximal direction along the longitudinal axis L3. The first latch pin 220a is movably supported in each of the first deck slots 106a, the first frame slot 214, and the first link slot 222. When the deck extension assembly 200 is in the retracted position R, the first latch pin 220a engages the first proximal deck notch 108a. When the deck extension assembly 200 is in the extended position E, the first latch pin 220a engages the first distal deck notch 109a.

A force can be applied to the first latch link 218 to move the first latch link 218 relative to the deck extension frame 204 to simultaneously bring the first latch pin 220a out of engagement with the first proximal deck notch 108a and into the first deck slot 106a to allow movement of the deck extension frame 204 from the retracted position R towards the extended position E, or to simultaneously bring the first latch pin 220a out of engagement with the first distal deck notch 109a and into the first deck slot 106a to allow movement of the deck extension frame 204 from the extended position E towards the retracted position R.

As is illustrated in FIGS. 6 and 7, the deck extension assembly 200 may also include a second latch link (with a second card and a second link arm) and a second latch pin (not shown in detail). If included, the second latch link and the second latch pin 220b cooperate with: the second frame slot of the second extension rail 208b; and the second proximal deck notch 108b, the second deck slot 106b, and the second distal deck notch 109b of the second deck rail 100b to latch and release the deck extension assembly 200 in the extended position E or the retracted position R, and allow movement of the deck extension assembly 200 between the extended position E and the retracted position R. In some versions, the second link slot extends across the longitudinal axis L4 and has a second upper link slot end above the longitudinal axis L4 and a second lower link slot end below the longitudinal axis L4 (not shown in detail). In the illustrated versions, the second latch link comprises a second link slot formed in the second card, which has the second upper link slot end, and the second lower link slot end. (not shown in detail). The second link slot extends across the longitudinal axis L4 with the second upper link slot end above the longitudinal axis L4 in a proximal position and the second lower link slot end below the longitudinal axis L4 in a distal position (not shown in detail). In some versions, the second link slot extends across the longitudinal axis at a second angle of from 10° to 80° (not shown in detail). Further, the second latch link is moveably mounted to the deck extension frame 204. In the illustrated versions, the second latch link is coupled to the proximal second rail end of the second extension rail 208b. The second latch link is coupled to the second extension rail 208b with a second biasing element, e.g., a spring. In this example, the second latch link is biased in a proximal direction along the longitudinal axis L4. The second latch pin 220b is movably supported in each of the second deck slots 106b, the second frame slot, and the second link slot. When the deck extension assembly 200 is in the retracted position R, the second latch pin 220b engages the second proximal deck notch 108b. When the deck extension assembly 200 is in the extended position E, the second latch pin 220b engages the second distal deck notch 109b.

In such examples, a force can be applied to the second latch link to move the second latch link relative to the deck extension frame 204 to simultaneously bring the second latch pin 220b out of engagement with the second proximal deck notch 108b and into the second deck slot 106b to allow movement of the deck extension frame 204 from the retracted position R towards the extended position E, or to simultaneously bring the second latch pin 220b out of engagement with the second distal deck notch 109b and into the second deck slot 106b to allow movement of the deck extension frame 204 from the extended position E towards the retracted position R.

In some versions, the deck extension assembly 200 includes an engagement member 230, a handle cam 231, a hinged cross-mount 232, first and second end cams 233, 234, a handle 238, and a handle mount 239. The engagement member 230 defines an axis of rotation AR. Here, the deck extension frame 204 comprises engagement member mounts 240 supporting bushings 242 which, in turn, receive the engagement member 230 along the axis of rotation AR. The handle mount 239 is coupled to the deck extension frame 204 and slidably supports the handle 238 for longitudinal movement. The handle cam 231 is coupled to the engagement member 230 for concurrent movement about the axis of rotation AR. Similarly, the first and second end cams 233, 234 are likewise coupled to the engagement member 230 for concurrent movement about the axis of rotation AR. The hinged cross-mount 232 is pivotably coupled between the handle 238 and the handle cam 231. The first end cam 233 is pivotably coupled to the first link arm 221 of the first latch link 218. With this arrangement, force applied to the handle 238 which effects sliding movement of the handle 238 relative to the handle mount 239 results in pivoting movement of the hinged cross-mount 232 which, in turn, moves the handle cam 231 to rotate the engagement member 230 about the axis of rotation AR which, in turn, moves the first end cam 233 so as to move the first link arm 221 and the first card 219 of the first latch link 218 along the longitudinal axis L3.

In the illustrated versions, the first end cam 233 of the engagement member 230 includes a first leg 236 having a first foot 237 that is radially off set from the axis of rotation AR and connected to the first link arm 221 of the first latch link 218. Actuation of the handle 238, and the in-turn rotation of the engagement member 230, drives the first latch link 218 in a distal direction along the longitudinal axis L3 and the first latch pin 220a out of either the first proximal deck notch 108a or the first distal deck notch 109a of the first deck rail 100a to allow extension or retraction of the deck extension frame 204.

In this example, the force applied to the first latch link 218 via the handle 238 moves the first latch link 218 relative to the deck extension frame 204 in a distal direction along the longitudinal axis L3, which drives the first latch pin 220a from the first lower link slot end 226 to the first upper link slot end 224, from the lower end of the first frame slot 214 to the upper end of the first frame slot 214, out of either the first proximal deck notch 108a or the first distal deck notch 109a of the first deck rail 100a to allow extension or retraction of the deck extension assembly 200.

In the illustrated versions, force applied to the handle 238 rotates the engagement member 230 about the axis of rotation AR, which also moves the second latch link along the longitudinal axis L4. In the illustrated versions, movement of the handle 238 results in rotation of the engagement member 230 about the axis of rotation AR defined thereby. In the illustrated versions, the second end cam 234 of the engagement member 230 includes a second leg having a second foot that is radially off set from the axis of rotation AR and connected to the second latch link. Actuation of the handle 238, and the in-turn rotation of the engagement member 230 drives the second latch link in a distal direction along the longitudinal axis L4 and the second latch pin 220b out of either the second proximal deck notch 108b or the second distal deck notch 109b of the second deck rail 100b to allow extension or retraction of the deck extension frame 204.

The deck extension assembly 200 is latched in the retracted or extended position E by the movement of the first latch pin 220a within the 3 slots: (1) the first frame slot 214 of the first extension rail 208a; (2) the first proximal deck notch 108a, the first deck slot 106a, and the first distal deck notch 109a of the first deck rail 100a; and (3) the first link slot 222 of the first card 219 of the first latch link 218. In the examples illustrated, the first link slot 222 defined in the first card 219, which is arranged at the distal end of the first latch link 218. In some versions, the first link slot 222 slot extends across the longitudinal axis L3 and has the first upper link slot end 224 above the longitudinal axis L3 and a first lower link slot end 226 below the longitudinal axis L3. In the illustrated versions, the first link slot 222 extends across the longitudinal axis L3 with the first upper link slot end 224 above the longitudinal axis L3 in a proximal position and the first lower link slot end 226 below the longitudinal axis L3 in a distal position. However, it should also be appreciated that in some examples the first link slot 222 can extend across the longitudinal axis L3 with the first upper link slot end 224 above the longitudinal axis L3 in a distal position and the first lower link slot end 226 below the longitudinal axis L3 in a proximal position.

In the illustrated versions, the first upper link slot end 224 having an oblique a first angle A1 coupled with the movement of the first latch link 218 is what drives the first latch pin 220a out of the first proximal deck notch 108a (or the first distal deck notch 109a) of the first deck rail 100a and into the first deck slot 106a in order to allow the movement of the deck extension assembly 200. To this end, various parameters such as: the orientation of the first proximal deck notch 108a and the first distal deck notch 109a (e.g., extending downward from the longitudinal axis L3, extending upward from the longitudinal axis L3, etc.) of the first deck rail 100a, the movement of the first latch link 218 (e.g., in a proximal or distal direction), the direction in which the first biasing element 228 biases the first latch link 218, and the like can be changed to accomplish the same results. For example, if the first latch link 218 is configured to move in a distal direction along a longitudinal axis, and the first proximal deck notch 108a and the first distal deck notch 109a extending upward (towards the support surface) from the longitudinal axis L3, then the first link slot 222 can extend across the longitudinal axis L3 with the first upper link slot end 224 above the longitudinal axis L3 in a distal position and the first lower link slot end 226 below the longitudinal axis L3 in a proximal position so that movement of the first latch link 218 drives the first latch pin 220a downward and out of the first proximal deck notch 108a or the first distal deck notch 109a and out into the first deck slot 106a so that the deck extension assembly 200 can be moved between the extended and retracted positions E, R.

As another example, if the first latch link 218 is configured to move in a proximal direction along a longitudinal axis, and the first proximal deck notch 108a and the first distal deck notch 109a extending downward (towards the floor) from the longitudinal axis L3, then the first link slot 222 can extend across the longitudinal axis L3 with the first upper link slot end 224 above the longitudinal axis L3 in a distal position and the first lower link slot end 226 below the longitudinal axis L3 in a proximal position so that movement of the first latch link 218 drives the first latch pin 220a upward and out of the first proximal deck notch 108a or the first distal deck notch 109a and out into the first deck slot 106a so that the deck extension assembly 200 can be moved between the extended and retracted positions E, R.

In the illustrated versions, sliding movement of the deck extension assembly 200 is facilitated by deck rollers 246 and slide bushings 248 coupled to the first and second deck rails 100a, 100b, as well as by frame rollers 250 coupled to the first and second extension rails 208a, 208b (see FIG. 7).

Many of the components of the deck extension assembly 200 are described as a "first" component or a "second" component depending on what side of the bed they are located on. It should be appreciated that the components can be configured to function on either side or both sides of the deck extension assembly 200.

Figure 8:
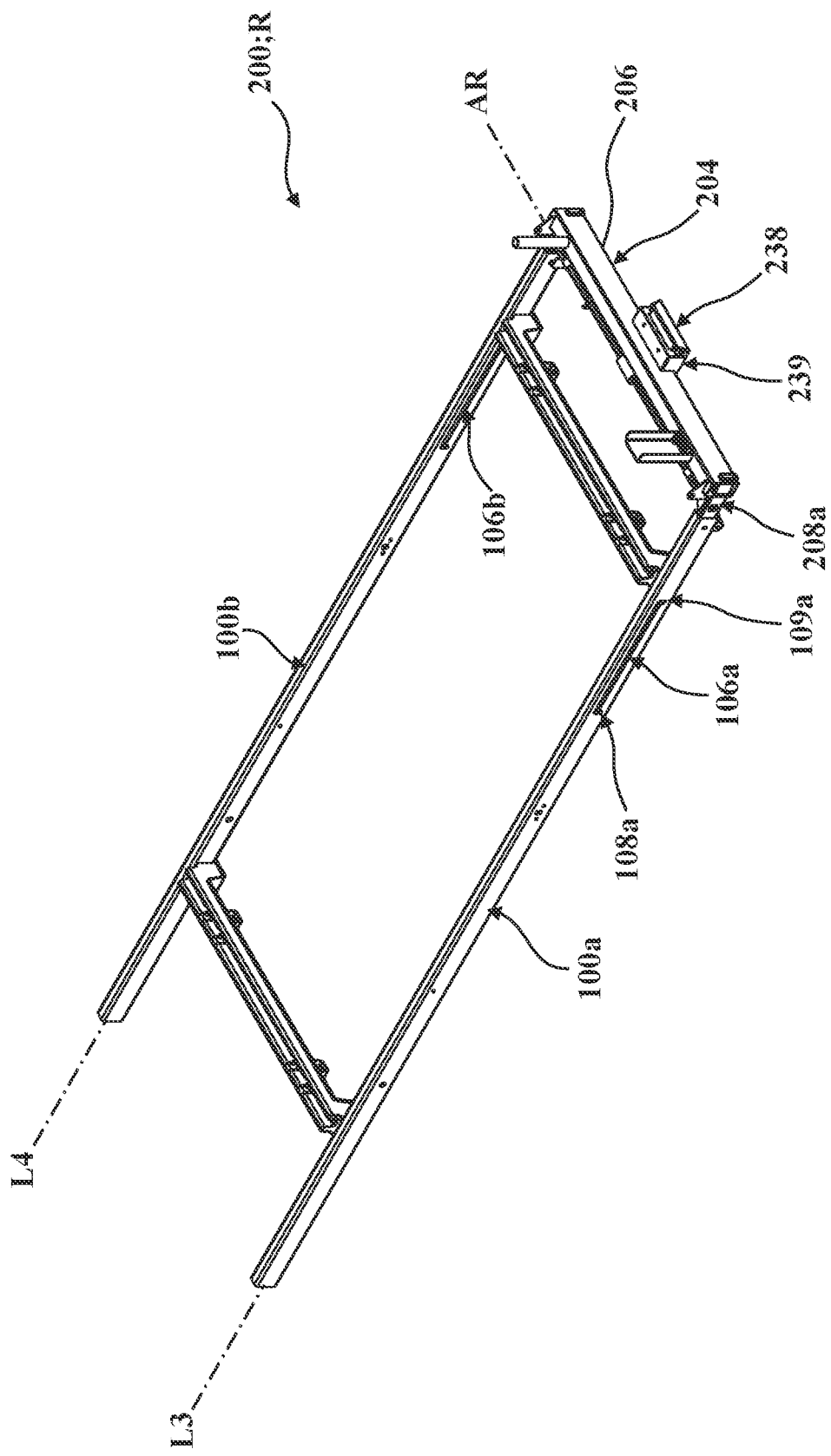
FIG. 8 is a perspective view of a deck extension frame of an example deck extension assembly latched in the retracted position.

In FIG. 8, the deck extension assembly 200 is latched in the retracted position R. Here, the first latch pin 220a is movably supported in each of the first deck slot 106a, the first frame slot 214, and the first link slot 222. With the deck extension assembly 200 in the retracted position R, the first latch pin 220a is engaged in the first proximal deck notch 108a, which prevents the movement/extension of the deck extension assembly 200.

Figure 9:
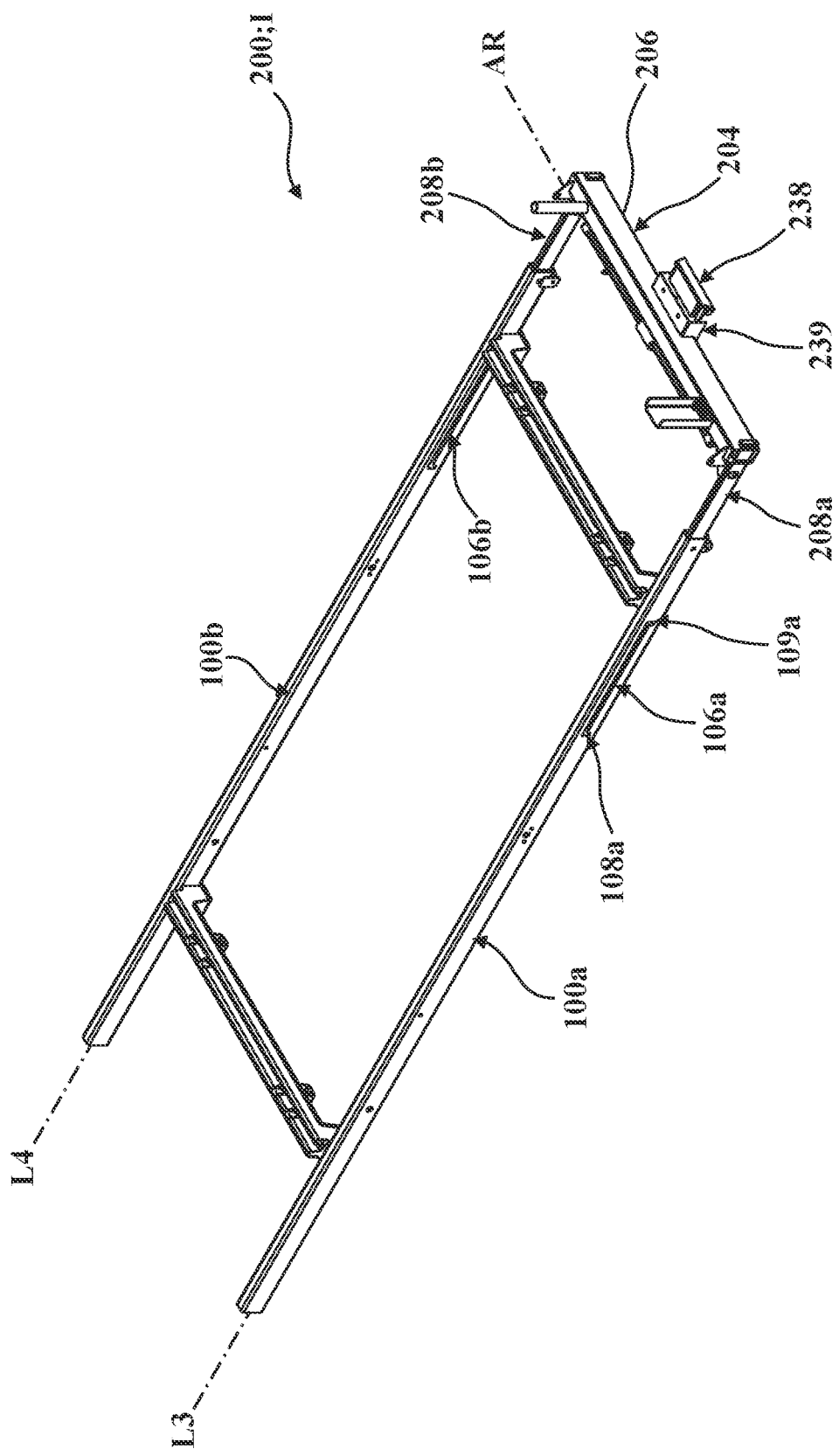
FIG. 9 is a perspective view of the deck extension frame of the example deck extension assembly of FIG. 8 moveable in an intermediate position.

In FIG. 9, the deck extension assembly 200 is arranged in an intermediate position I. Here, a user has actuated the handle 238, and the force applied to the first latch link 218 via the handle 238 has moved the first latch link 218 relative to the deck extension frame 204 in a distal direction along the longitudinal axis L3, which drives the first latch pin 220a from the first lower link slot end 226 to the first upper link slot end 224 and out of the first proximal deck notch 108a of the first deck rail 100*a* to allow movement/extension of the deck extension frame 204. Here in FIG. 9, the first latch pin 220*a* is in the first deck slot 106*a* and thus freely moveable towards either the extended position E or the retracted position R.

Figure 10:
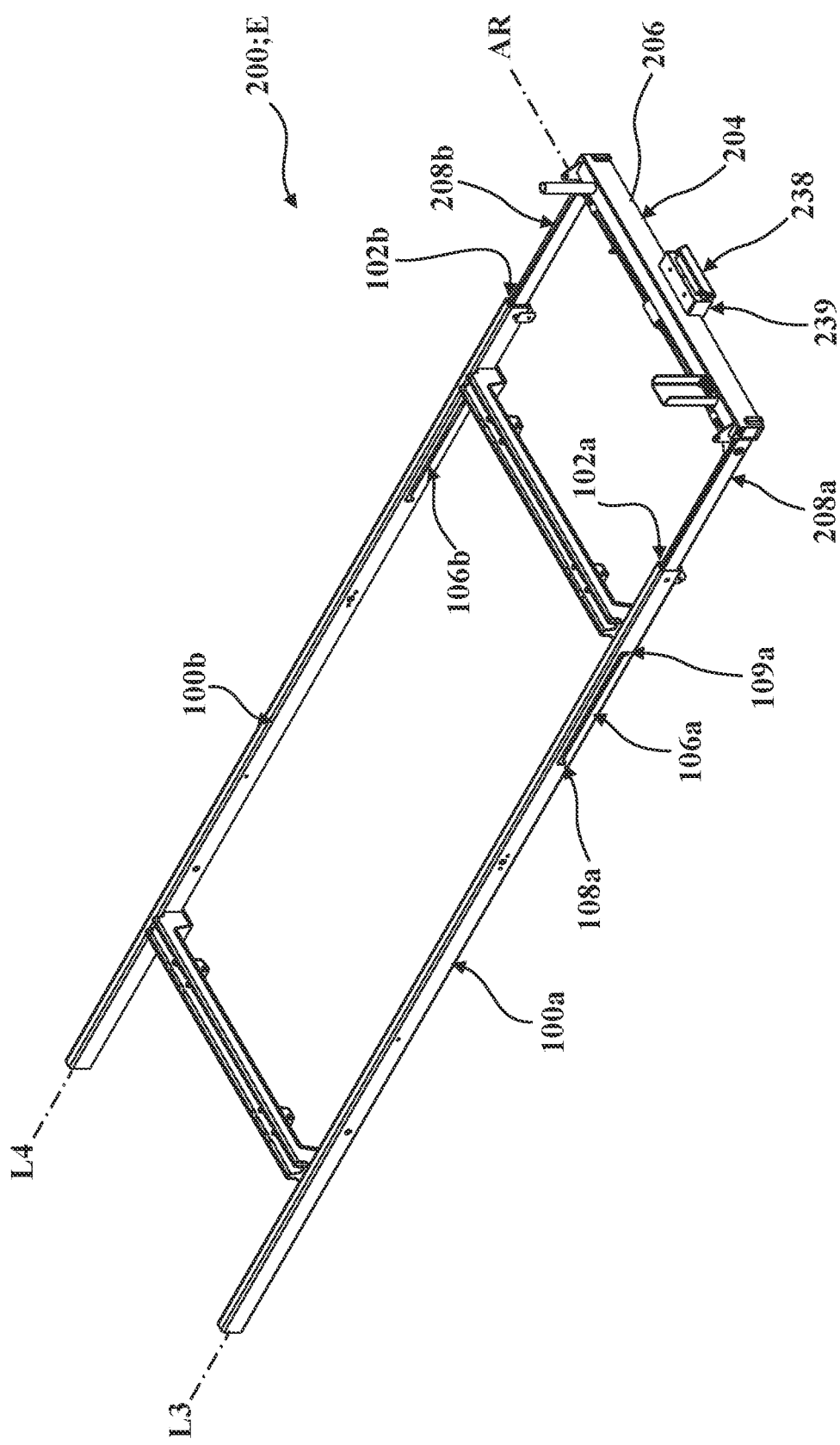
FIG. 10 is a perspective view of the deck extension frame of the example deck extension assembly of FIGS. 8 and 9 latched in an extended position.

In FIG. 10, the deck extension assembly 200 is latched in an extended position E. Here, the first latch link 218 is in first distal deck notch 109*a* of the first deck rail 100*a* and deck extension assembly 200 is latched in position. To unlatch the deck extension assembly 200, a force would have to be applied to the first latch link 218 via the handle 238 to the first latch link 218 relative to the deck extension frame 204 in a distal direction along the longitudinal axis L3, which drives the first latch pin 220*a* from the first lower link slot end 226 to the first upper link slot end 224 and out of the first distal deck notch 109*a* of the first deck rail 100*a* to allow movement/retraction of the deck extension frame 204.

Figure 11:
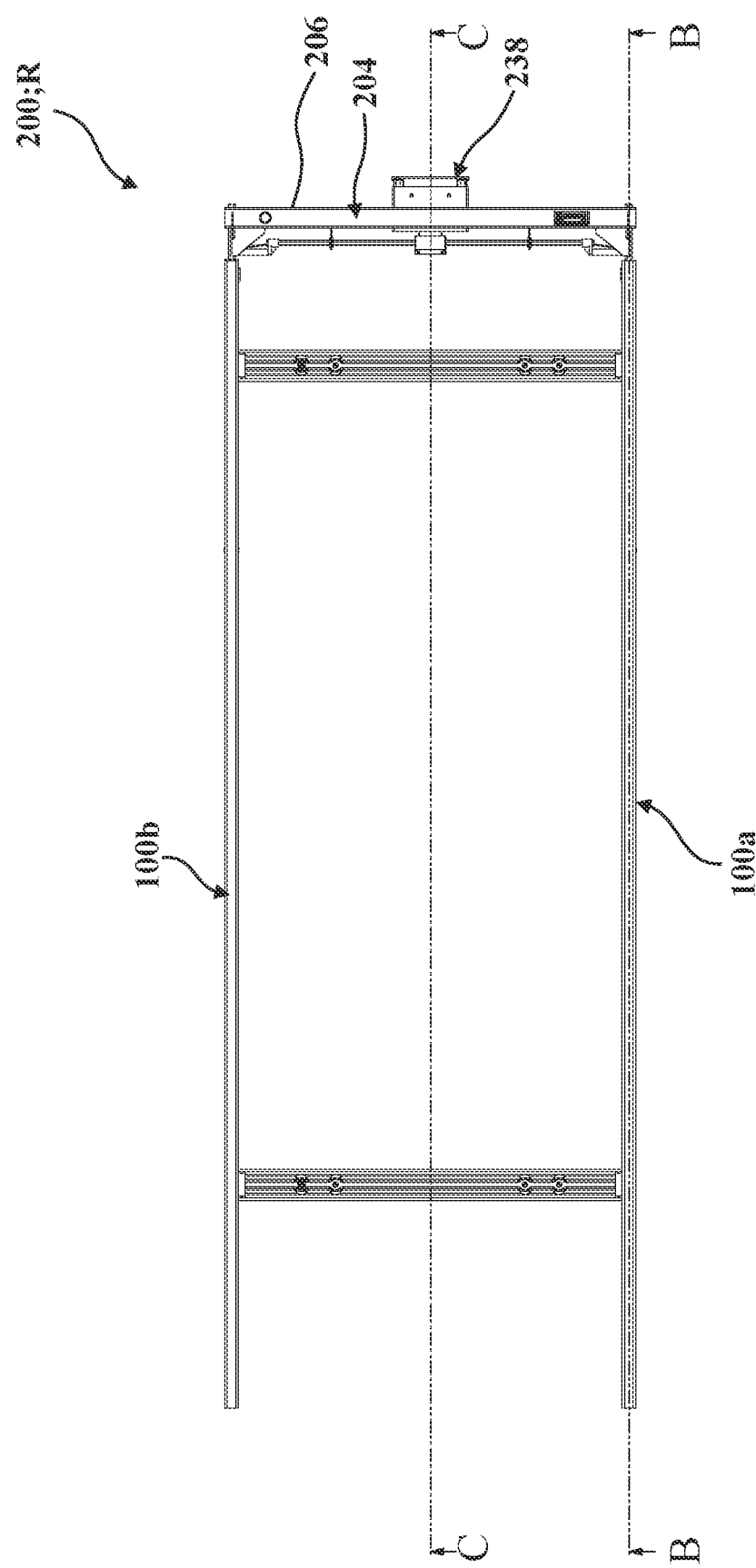
FIG. 11 is a top perspective view of the deck extension frame of the example deck extension assembly of FIG. 8.

In FIG. 11 a top perspective view of the deck extension frame 204 of the deck extension assembly 200 is illustrated. Various side and cross-sectional views along B-B and C-C of the deck extension assembly 200 are illustrated in FIGS. 12A-16C to help show the movement of the deck extension assembly 200 from the retracted position R to the extended position E.

In FIGS. 12A-12C, the first latch pin 220*a* is movably supported in each of the first deck slot 106*a*, the first frame slot 214, and the first link slot 222. With the deck extension assembly 200 in the retracted position R, the first latch pin 220*a* is engaged in the first proximal deck notch 108*a*, which prevents the movement/extension of the deck extension assembly 200.

In FIG. 12A, a side view of the first deck rail 100*a* is illustrated. In this example, the first deck slot 106*a* extends parallel to the longitudinal axis L3 and the first proximal deck notch 108*a* and the first distal deck notch 109*a* extend downward the first deck slot 106*a* (towards the floor) and perpendicular to the longitudinal axis L3. The first latch pin 220*a* is engaged with the first proximal deck notch 108*a* being located at the lower end of the first distal deck notch 109*a*, which prevents movement/extension of the deck extension assembly 200.

FIG. 12B is a cross-sectional view taken along B-B. With this illustration, the outer wall of the first deck rail 100*a* is not shown so the first latch pin 220*a*, which is engaged in the first proximal deck notch 108*a*, is also clearly illustrated in the first lower link slot end 226 of the first link slot 222, which extends across the longitudinal axis L3 with the first upper link slot end 224 above the longitudinal axis L3 in a proximal position and the first lower link slot end 226 below the longitudinal axis L3 in a distal position. Here, it will be appreciated that the distal movement of the first latch link 218 will drive the first latch pin 220*a* the first upper link slot end 224 above the longitudinal axis L3, out of the first proximal deck notch 108*a*, and into the first deck slot 106*a* to allow the movement of the deck extension assembly 200.

In FIG. 12C, a cross-sectional view along C-C is illustrated. In this example, the second deck slot 106*b* extends parallel to the longitudinal axis L4 and the second proximal deck notch 108*b* and the second distal deck notch 109*b* extend downward from the second deck slot 106*b* (towards the floor) and perpendicular to the longitudinal axis L4. The second latch pin 220*b* is engaged with the second proximal deck notch 108*b* being located at the lower end of the second distal deck notch 109*b*, which prevents movement/extension of the deck extension assembly 200.

As described above, the first deck slot 106*a* extends parallel to the longitudinal axis L3 and the first proximal deck notch 108*a* and the first distal deck notch 109*a* extend downward the first deck slot 106*a* (towards the floor) and perpendicular to the longitudinal axis L3. As noted above, the first deck slot 106*a*, the first proximal deck notch 108*a*, and the first distal deck notch 109*a* are defined through the inner and outer walls of the first deck rail 100*a*. Accordingly, FIG. 12A provides a view of the outer wall of the first deck rail 100*a*, while FIG. 12C provides a view of the inner wall of the second deck rail 100*b*.

In FIG. 13A, a side view of the first deck rail 100*a* is illustrated. In this example, the first deck slot 106*a* extends parallel to the longitudinal axis L3 and the first proximal deck notch 108*a* and the first distal deck notch 109*a* extend downward the first deck slot 106*a* (towards the floor) and perpendicular to the longitudinal axis L3. The first latch pin 220*a* is engaged with the first proximal deck notch 108*a* but has been driven upward and is located at the upper end of the first distal deck notch 109*a* and is thus free to move into the first deck slot 106*a* to allow the movement of the deck extension assembly 200.

FIG. 13B is a cross-sectional view taken along B-B. With this illustration, the outer wall of the first deck rail 100*a* is not shown so the first latch pin 220*a*, which is in the first proximal deck notch 108*a*, is also illustrated in the first upper link slot end 224 above the longitudinal axis L3 in a proximal position. Here, it will be appreciated that the distal movement of the first latch link 218 drives the first latch pin 220*a* to the first upper link slot end 224 to allow the movement of the deck extension assembly 200.

In FIG. 13C, a cross-sectional view along C-C is illustrated. In this example, the second deck slot 106*b* extends parallel to the longitudinal axis L4 and the second proximal deck notch 108*b* and the second distal deck notch 109*b* extend downward the second deck slot 106*b* (towards the floor) and perpendicular to the longitudinal axis L4. The second latch pin 220*b* is engaged with the second proximal deck notch 108*b* but has been driven upward and is located at the upper end of the second distal deck notch 109*b* and is thus free to move into the second deck slot 106*b* to allow the movement of the deck extension assembly 200.

In FIG. 14A, a side view of the first deck rail 100*a* is illustrated. In this example, the first deck slot 106*a* extends parallel to the longitudinal axis L3 and the first proximal deck notch 108*a* and the first distal deck notch 109*a* extend downward from the first deck slot 106*a* (towards the floor) and perpendicular to the longitudinal axis L3. The first latch pin 220*a* is engaged in the first deck slot 106*a* and the deck extension assembly 200 is in an intermediate position as the deck extension assembly 200 is being moved/extended.

FIG. 14B is a cross-sectional view taken along B-B. With this illustration, the outer wall of the first deck rail 100*a* is not shown so the first latch pin 220*a*, which is in the first deck slot 106*a*, is also illustrated in the first upper link slot end 224 above the longitudinal axis L3. Here, it will be appreciated that the distal movement the deck extension assembly 200 occurred as a user pulled the handle 238 in a distal direction along the longitudinal axis L3.

In FIG. 14C, a side view of the second deck rail 100*b* is illustrated. In this example, the second deck slot 106*b* extends parallel to the longitudinal axis L4 and the second proximal deck notch 108*b* and the second distal deck notch 109*b* extend downward from the first deck slot 106*a* (towards the floor) and perpendicular to the longitudinal axis L4. The second latch pin 220*b* is engaged in the second deck slot 106*b* and the deck extension assembly 200 is in an intermediate position I as the deck extension assembly 200 is being moved/extended.

In FIG. 15A, a side view of the first deck rail 100a is illustrated. In this example, the first deck slot 106a extends parallel to the longitudinal axis L3 and the first proximal deck notch 108a and the first distal deck notch 109a extend downward the first deck slot 106a (towards the floor) and perpendicular to the longitudinal axis L3. The first latch pin 220a is engaged with the first distal deck notch 109a but is located at the upper end of the first distal deck notch 109a and is thus free to move down into the first distal deck notch 109a with the urging of the first biasing element 228 once the user lets go of the handle 238.

FIG. 15B is a cross-sectional view taken along B-B. With this illustration, the outer wall of the first deck rail 100a is not shown so the first latch pin 220a, which is in the first distal deck notch 109a, is also illustrated in the first upper link slot end 224 above the longitudinal axis L3 in a proximal position. Here, it will be appreciated that the release of the handle 238 in combination with the urging of the first biasing element 228 will force the first latch pin 220a into the first lower link slot end 226 and the lower end of the first distal deck notch 109a.

In FIG. 15C, a cross-sectional view along C-C is illustrated. In this example, the second deck slot 106b extends parallel to the longitudinal axis L4 and the second proximal deck notch 108b and the second distal deck notch 109b extend downward the second deck slot 106b (towards the floor) and perpendicular to the longitudinal axis L4. The second latch pin 220b is engaged with the second distal deck notch 109b, albeit in the upper end of the second distal deck notch 109b and is thus free to move into the lower end of the second distal deck notch 109b to latch the deck extension assembly 200 in the extended position E.

Figure 16A:
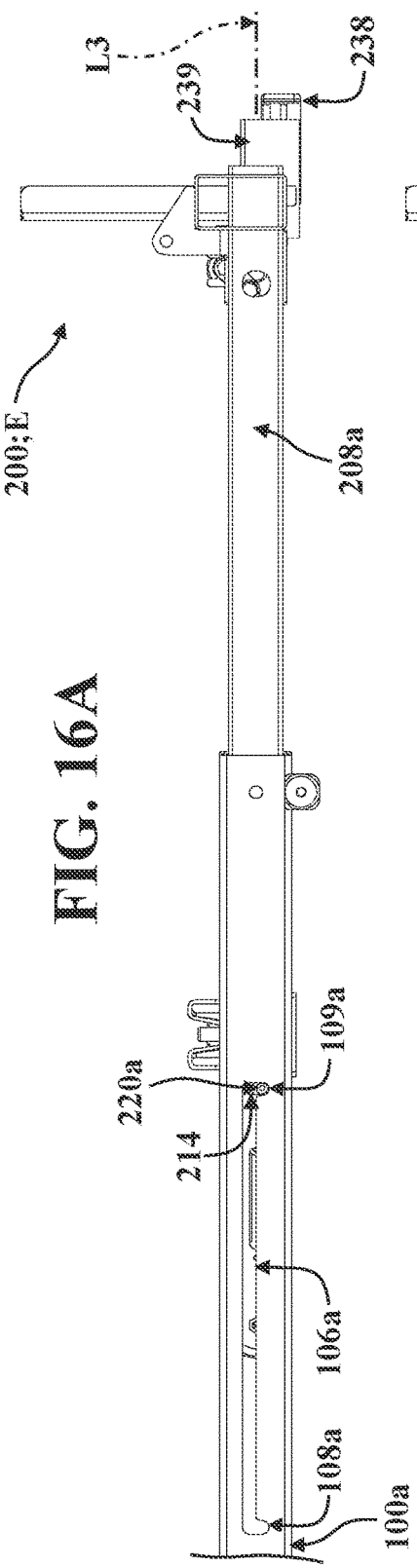
FIG. 16A a side view of the deck extension frame of the deck extension assembly of FIG. 11 latched in an extended position.

In FIG. 16A, a side view of the first deck rail 100a is illustrated. In this example, the first deck slot 106a extends parallel to the longitudinal axis L3 and the first proximal deck notch 108a and the first distal deck notch 109a extend downward the first deck slot 106a (towards the floor) and perpendicular to the longitudinal axis L3. The first latch pin 220a is engaged with the first distal deck notch 109a being located at the lower end of the first distal deck notch 109a, which prevents movement/extension of the deck extension assembly 200.

Figure 16B:
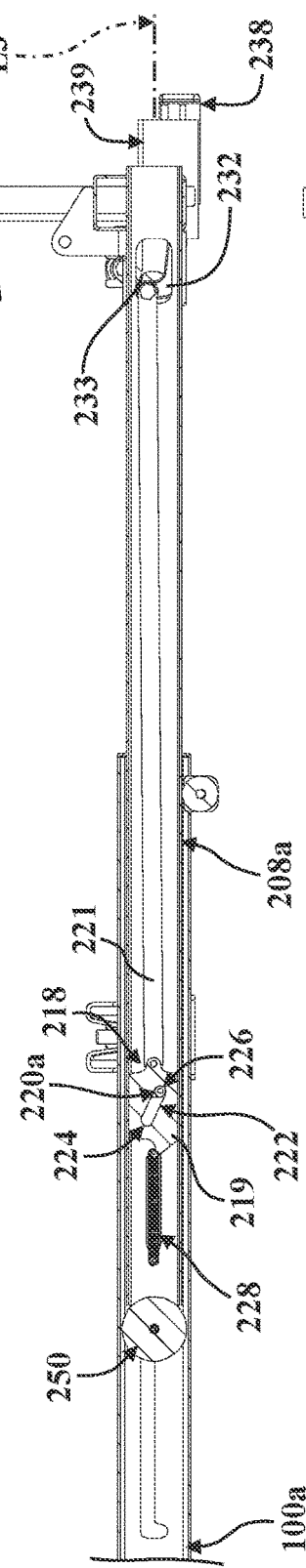
FIG. 16B a cross-sectional view along B-B of the deck extension frame of the deck extension assembly of FIG. 11 latched in an extended position.

FIG. 16B is a cross-sectional view taken along B-B. With this illustration, the outer wall of the first deck rail 100a is not shown so the first latch pin 220a, which is engaged in the first distal deck notch 109a, is also clearly illustrated in the first lower link slot end 226 of the first link slot 222 below the longitudinal axis L3 in a distal position. Here, it will be appreciated that the engagement of the first latch pin 220a in the first proximal deck notch 108a will prevent movement/retraction of the deck extension assembly 200. Here too, it will be appreciated that the distal movement of the first latch link 218 will drive the first latch pin 220a the first upper link slot end 224 above the longitudinal axis L3, out of the first distal deck notch 109a, and into the first deck slot 106a to allow the movement/retraction of the deck extension assembly 200.

Figure 16C:
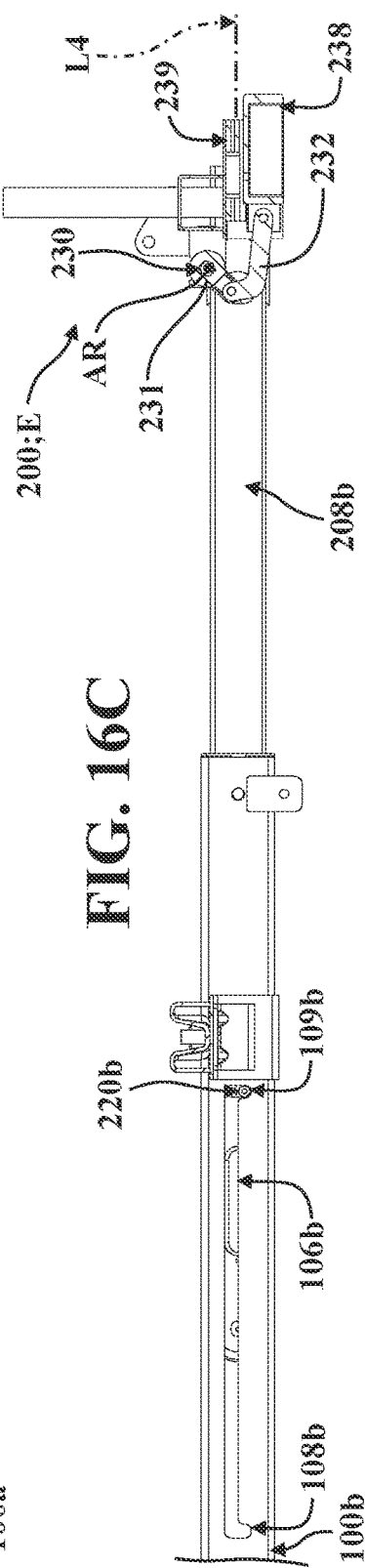
FIG. 16C a cross-sectional view along C-C of the deck extension frame of the deck extension assembly of FIG. 11 latched in an extended position.

In FIG. 16C, a cross-sectional view along C-C is illustrated. In this example, the second deck slot 106b extends parallel to the longitudinal axis L4 and the second proximal deck notch 108b and the second distal deck notch 109b extend downward from the second deck slot 106b (towards the floor) and perpendicular to the longitudinal axis L4. The second latch pin 220b is engaged with the second distal deck notch 109b being located at the lower end of the second distal deck notch 109b, which prevents movement/extension of the deck extension assembly 200.

Figure 20B:
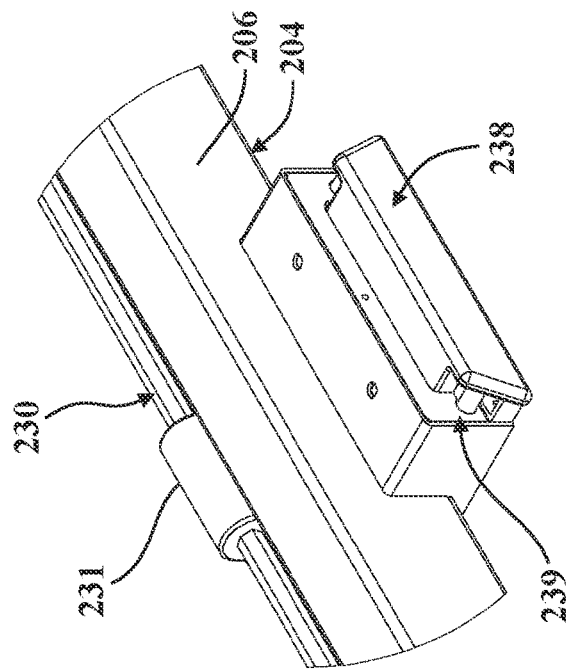
FIG. 20B is a first perspective view of the handle assembly of the deck extension assembly of FIG. 17 prior to actuation.
Figure 20A:
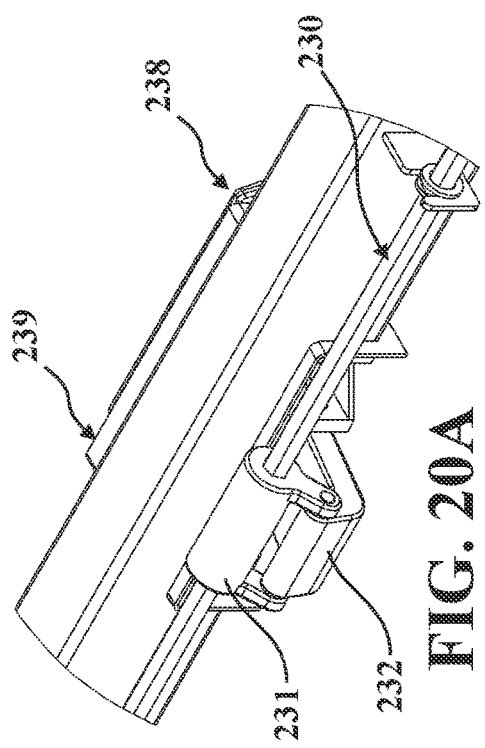
FIG. 20A a top perspective view of the deck extension frame of the deck extension assembly of FIG. 17 along A-A prior to actuation.

In FIG. 17 a top perspective view of the deck extension frame 204 of the deck extension assembly 200 is illustrated. In FIGS. 18 and 19 two different enlarged perspective views (A and B respectively) of the handle 238 are illustrated. In order to illustrate how force applied to the handle 238 results in the distal movement of the first latch link 218 along the longitudinal axis L3, which moves the first latch pin 220a and/or the second latch pin 220b into the first deck slot 106a and/or the second deck slot 106b to allow the movement of the deck extension assembly 200 between the retracted and extended positions R, E: FIGS. 20A, 21A, and 22A illustrate enlarged perspective views from A in FIG. 18; FIGS. 20B, 21B, and 22B illustrate enlarged perspective views from B in FIG. 19; and FIGS. 20C, 21C, and, 22C illustrate cross-sectional views of the handle along C-C of FIG. 17.

Figure 20C:
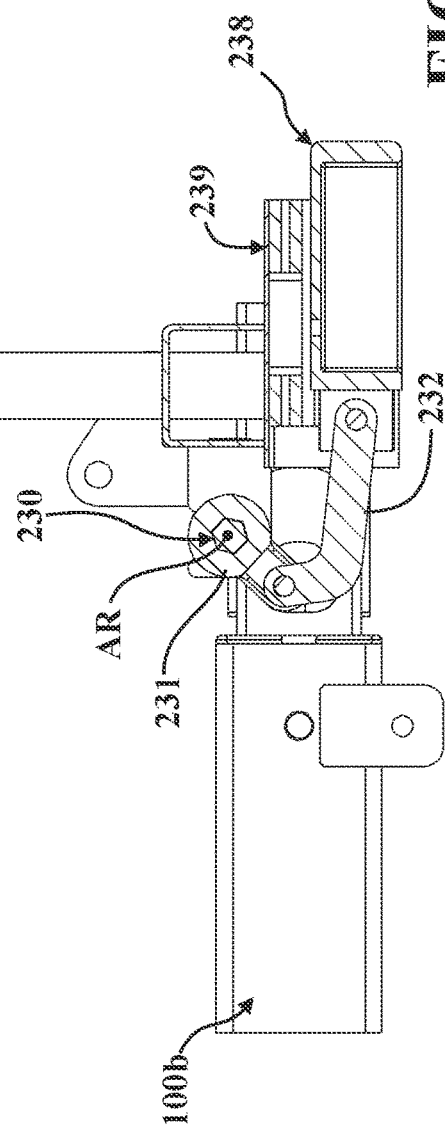
FIG. 20C is a second perspective view of the handle assembly of the deck extension assembly of FIG. 17 prior to actuation.
Figure 21B:
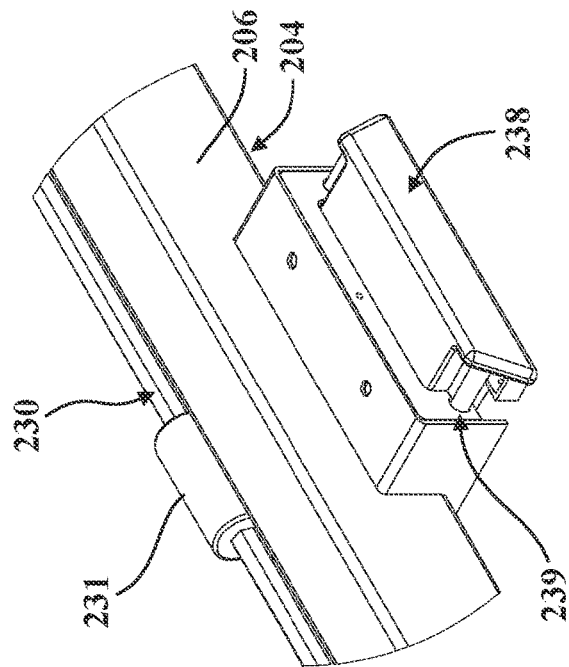
FIG. 21B is a first perspective view of the handle assembly of the deck extension assembly of FIG. 17 during actuation.
Figure 21A:
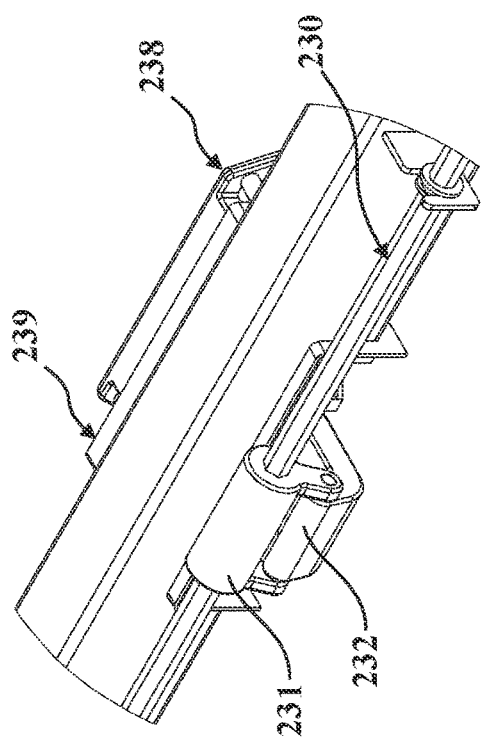
FIG. 21A a top perspective view of the deck extension frame of the deck extension assembly of FIG. 17 along A-A during actuation.

In FIGS. 20A-20C, the handle 238 is illustrated prior to actuation. The perspective view of FIG. 20A depicts the hinged cross-mount 232 and the handle cam 231 that connect the handle 238 to the engagement member 230. FIG. 20B shows the handle 238 and the handle cam 231 extending along the engagement member 230. FIG. 20C is a cross-sectional view along C-C which illustrates the position of the handle 238, the handle cam 231, the hinged cross-mount 232, and the engagement member 230 defining the axis of rotation AR.

Figure 21C:
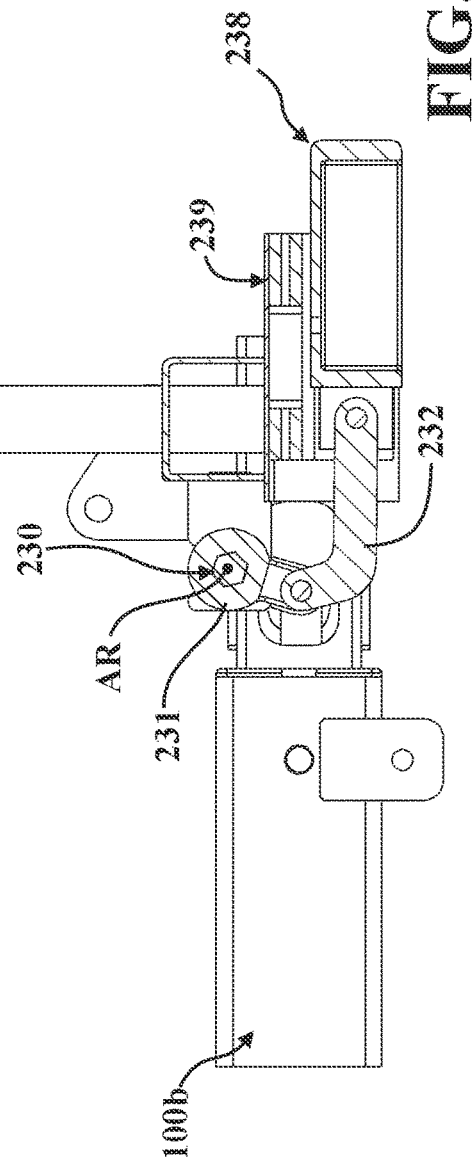
FIG. 21C is a second perspective view of the handle assembly of the deck extension assembly of FIG. 17 during actuation.
Figure 22B:
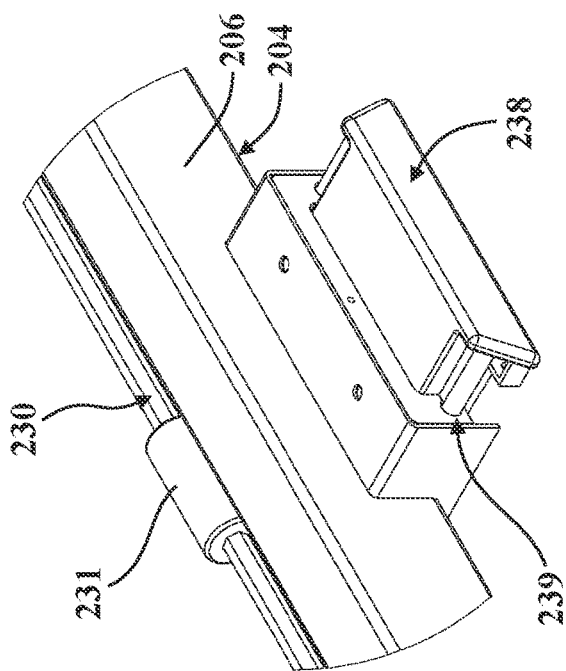
FIG. 22B is a first perspective view of the handle assembly of the deck extension assembly of FIG. 17 with the handle fully actuated.
Figure 22A:
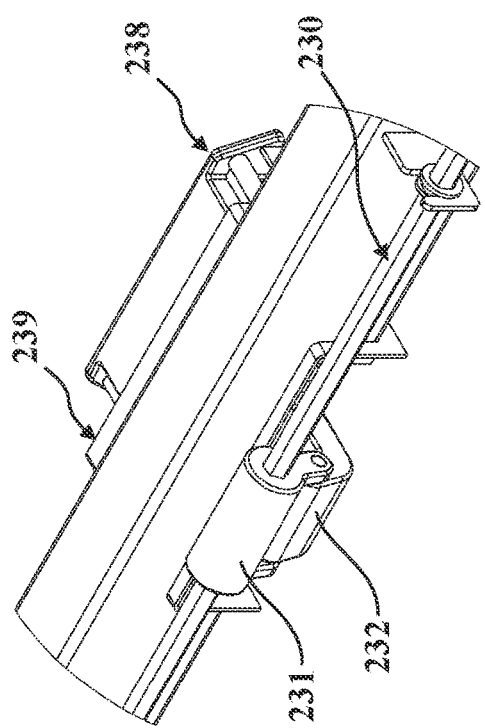
FIG. 22A a top perspective view of the deck extension frame of the deck extension assembly of FIG. 17 along A-A with the handle fully actuated.

In FIGS. 21A-21C, the handle 238 is depicted during actuation as a user pulls the handle 238, the hinged cross-mount 232 moves the handle cam 231 which, in turn, begins to rotate the engagement member 230 in a counter-clockwise direction around an axis of rotation AR. In unison, the engagement member 230 moves the first latch link 218 along the longitudinal axis L3 and/or the second latch link along the longitudinal axis L4 in a distal direction. In FIG. 21A, the hinged cross-mount 232 and the handle cam 231 are shown beginning to rotate the engagement member 230 in the counterclockwise direction around the axis of rotation AR. In FIG. 21B, the movement of the handle 238 in a distal direction is illustrated (i.e., the handle 238 is extended past its previous position in FIG. 20A). FIG. 21C is a cross-sectional view along C-C illustrating the position of the handle 238, the handle cam 231, the hinged cross-mount 232, and the engagement member 230.

Figure 22C:
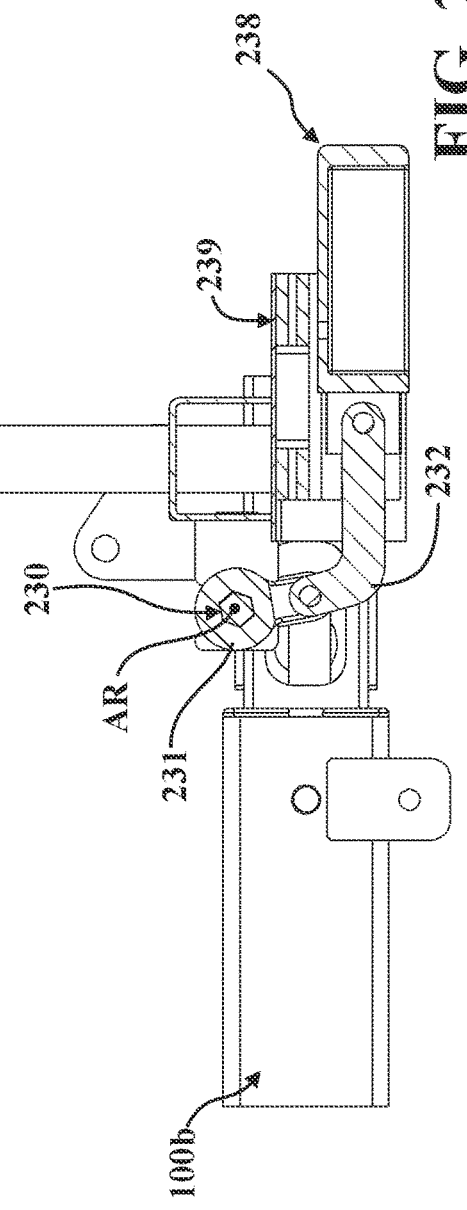
FIG. 22C is a second perspective view of the handle assembly of the deck extension assembly of FIG. 17 with the handle fully actuated.

In FIGS. 22A-22C, the handle 238 is illustrated in a fully actuated position which allows for the movement (extension or retraction) of the deck extension assembly 200. The hinged cross-mount 232 and the handle cam 231 have rotated the engagement member 230 further in the counter-clockwise direction around the axis of rotation AR to move the first latch link 218 along the longitudinal axis L3 and/or second latch link along the longitudinal axis L4 in a distal direction in order to place the first or the second latch pins 220a 220b in the first and second deck slots 106a, 106b to facilitate extension or retraction of the deck extension assembly 200. In FIG. 21A, the hinged cross-mount 232 is illustrated after rotation of the engagement member 230 in the counterclockwise direction around the axis of rotation AR. In FIG. 21B, the movement of the handle 238 in the distal direction along the longitudinal axis L2 is illustrated (i.e., the handle 238 is extended past its previous position in FIG. 21A). FIG. 21C is a cross-sectional view along C-C illustrating the position of the handle 238, the handle cam 231, the hinged cross-mount 232, the engagement member 230 with the handle 238 actuated.

It is to be appreciated that the terms "include," "includes," and "including" have the same meaning as the terms "comprise," "comprises," and "comprising."

Several versions have been discussed in the foregoing description. However, the versions discussed herein are not intended to be exhaustive or limit the invention to any form. The terminology which has been used is intended to be in the nature of words of description rather than of limitation. Many modifications and variations are possible considering the above teachings and the invention may be practiced otherwise than as specifically described.

What is claimed is:

1. A patient support apparatus comprising:
a support frame including a deck rail defining a channel disposed about a longitudinal axis and having a deck slot extending between a proximal deck notch and a distal deck notch;
a patient support deck carried by the support frame and comprising a plurality of sections including a foot section;
a deck extension assembly including a deck extension section supported by a deck extension frame including an extension rail moveably disposed in the channel and having a frame slot, the deck extension assembly being selectively movable between an extended position to support the patient, and a retracted position;
a latch link comprising a link slot and being moveably mounted to the deck extension frame; and
a latch pin arranged for movement along each of the deck slot, the frame slot, and the link slot, wherein the latch pin engages the proximal deck notch when the deck extension assembly is in the retracted position and engages the distal deck notch when the deck extension assembly is in the extended position, and
wherein force applied to the latch link moves the latch link relative to the deck extension frame to simultaneously bring the latch pin out of engagement with the proximal deck notch and into the deck slot to allow movement of the deck extension frame from the retracted position towards the extended position, or to simultaneously bring the latch pin out of engagement with the distal deck notch and into the deck slot to allow movement of the deck extension frame from the extended position towards the retracted position.

2. The patient support apparatus of claim 1, wherein a proximal link end of the latch link is coupled to a proximal rail end of the extension rail.

3. The patient support apparatus of claim 1, wherein the latch link is coupled to the extension rail with a biasing element.

4. The patient support apparatus as set forth in claim 3, wherein the latch link is biased in a proximal direction along the longitudinal axis.

5. The patient support apparatus as set forth in claim 1, further comprising a handle and an engagement member defining an axis of rotation, wherein force applied to the handle rotates the engagement member, which moves the latch link along the longitudinal axis.

6. The patient support apparatus as set forth in claim 5, further comprising a cross-mount that connects the handle to the engagement member, wherein movement of the handle results in rotation of the engagement member about the axis of rotation defined thereby.

7. The patient support apparatus as set forth in claim 6, wherein an end of the engagement member includes a leg having a foot that is radially off set from the axis of rotation and connected to the latch link, wherein rotation of the engagement member drives the latch link in a distal direction along the longitudinal axis and the latch pin out of either the proximal deck notch or the distal deck notch of the deck rail to allow extension or retraction of the deck extension frame.

8. The patient support apparatus as set forth in claim 7, wherein the deck extension frame comprises one or more engagement member mounts defining an opening shaped to receive the engagement member.

9. The patient support apparatus as set forth in claim 1, wherein the deck rail comprises a deck roller in contact with the extension rail.

10. The patient support apparatus as set forth in claim 1, wherein the deck rail has an inner wall and an outer wall, and the deck slot is defined by the inner wall and/or the outer wall.

11. The patient support apparatus as set forth in claim 1, wherein the deck slot extends parallel to the longitudinal axis and the proximal deck notch and the distal deck notch extend perpendicular to longitudinal axis.

12. The patient support apparatus as set forth in claim 11, wherein the link slot extends across the longitudinal axis and has an upper end above the longitudinal axis and a lower end below the longitudinal axis.

13. The patient support apparatus as set forth in claim 12, wherein the link slot extends across the longitudinal axis at an angle of from 10° to 80°.

14. The patient support apparatus as set forth in claim 13, wherein movement of the latch link relative to the deck extension frame simultaneously forces the latch pin from the lower end of the link slot to the upper end of the link slot and out of the proximal deck notch and into the deck slot to allow movement of the deck extension frame between the retracted position and the extended position.

15. The patient support apparatus as set forth in claim 12, wherein the frame slot extends perpendicular to the longitudinal axis and has an upper and a lower end.

16. The patient support apparatus as set forth in claim 15, wherein force applied to the latch link moves the latch link relative to the deck extension frame in a distal direction along the longitudinal axis, which drives the latch pin from the lower end of the link slot to the upper end of the link slot, from the lower end of the frame slot to the upper end of the frame slot, and out of the proximal deck notch or the distal deck notch and into the deck slot to allow extension or retraction of the deck extension frame.

17. The patient support apparatus as set forth in claim 1, comprising a second latch link operable for actuation via a handle to move relative to a second deck rail to simultaneously force a second latch pin out of a second proximal deck notch and into a second deck slot to allow movement of the deck extension frame between the retracted and extended positions, wherein the second latch link is opposite the latch link and wherein actuation of the second latch link is simultaneous with actuation of the latch link via the handle to allow movement of the deck extension frame between the retracted and extended positions.

18. A patient support apparatus comprising:
a support frame including a deck rail defining a channel and having a deck slot extending along the deck rail between a proximal deck notch and a distal deck notch each disposed in communication with the deck slot;
a patient support deck carried by the support frame and comprising a plurality of sections including a foot section;
a deck extension assembly including a deck extension section supported by a deck extension frame including an extension rail moveably disposed in the channel and having a frame slot, the deck extension assembly being selectively movable along a longitudinal rail axis between an extended position to support of the patient, and a retracted position;

a latch link comprising a link slot and being moveably mounted to the deck extension frame; and a latch pin movably supported in each of the deck slot, the frame slot, and the link slot;

wherein the latch pin engages the proximal deck notch when the deck extension assembly is in the retracted position and engages the distal deck notch when the deck extension assembly is in the extended position, and wherein force applied to the latch link moves the latch link relative to the deck extension frame, and the link slot is arranged at an oblique angle relative to the longitudinal rail axis such that movement of the latch link drives the latch pin vertically and out of the proximal deck notch or the distal deck notch and into the deck slot to allow movement of the deck extension frame between the retracted and extended positions.

19. The patient support apparatus as set forth in claim 18, wherein movement of the latch link relative to the deck extension frame in a distal direction simultaneously forces the latch pin within the link slot and out of the proximal deck notch and into the deck slot to allow movement of the deck extension frame between the retracted and extended positions.

20. A patient support apparatus comprising:

a support frame including a deck rail defining a channel disposed about a longitudinal axis and having a deck guide extending between a proximal deck brace and a distal deck brace;

a patient support deck carried by the support frame and comprising a plurality of sections;

a deck extension assembly including a deck extension section supported by a deck extension frame including an extension rail moveably disposed in the channel and having a frame guide, the deck extension assembly being selectively movable between an extended position and a retracted position;

a latch link comprising a link guide and being moveably mounted to the deck extension frame; and a latch pin arranged for movement along each of the deck guide, the frame guide, and the link guide, wherein the latch pin engages the proximal deck brace when the deck extension assembly is in the retracted position and engages the distal deck brace when the deck extension assembly is in the extended position, and wherein force applied to the latch link moves the latch link relative to the deck extension frame to simultaneously bring the latch pin out of engagement with the proximal deck brace and into engagement with the deck guide to allow movement of the deck extension frame from the retracted position towards the extended position along the deck guide, or to simultaneously bring the latch pin out of engagement with the distal deck brace and into engagement with the deck guide to allow movement of the deck extension frame from the extended position towards the retracted position.

* * * * *